United States Patent [19]

Levy

[11] Patent Number: 4,985,251
[45] Date of Patent: Jan. 15, 1991

[54] FLOWABLE INSECTICIDAL DELIVERY COMPOSITIONS AND METHODS FOR CONTROLLING INSECT POPULATIONS IN AN AQUATIC ENVIRONMENT

[75] Inventor: Richard Levy, Fort Meyers, Fla.

[73] Assignee: Lee County Mosquito Control District, Fort Meyers, Fla.

[21] Appl. No.: 210,801

[22] Filed: Jun. 24, 1988

Related U.S. Application Data

[63] Continuation-in-part of Ser. No. 32,532, Apr. 1, 1987, Pat. No. 4,818,534.

[51] Int. Cl.$^5$ .................... A01N 25/34; A61K 9/14
[52] U.S. Cl. .................... 424/404; 424/405; 424/408; 424/409; 424/78; 424/84; 424/410
[58] Field of Search .................... 424/405, 408, 78, 84, 424/410, 409; 71/3

[56] References Cited

U.S. PATENT DOCUMENTS

| | | | |
|---|---|---|---|
| 3,085,850 | 4/1963 | Egan et al. | 21/60.5 |
| 3,415,614 | 10/1968 | Egan et al. | 21/60.5 |
| 3,535,423 | 10/1970 | Ordas | 424/176 |
| 3,576,760 | 4/1971 | Gould et al. | 424/487 X |
| 3,957,480 | 5/1976 | Kornis | 424/405 X |
| 4,053,627 | 10/1977 | Scher | 424/278 |
| 4,058,124 | 11/1977 | Yen et al. | 424/79 |
| 4,062,855 | 12/1977 | Allan et al. | 424/78 |
| 4,070,348 | 1/1978 | Kraemer et al. | 424/404 X |
| 4,110,431 | 8/1978 | Oita | 424/78 |
| 4,134,863 | 1/1979 | Fanta et al. | 128/285 |
| 4,154,818 | 5/1979 | Kanada et al. | 424/81 |
| 4,160,033 | 7/1979 | Garrett et al. | 424/285 |
| 4,182,620 | 1/1980 | Denninger et al. | 71/65 |
| 4,244,728 | 1/1981 | DelliColli et al. | 424/405 X |
| 4,267,280 | 5/1981 | McCormick | 525/56 |
| 4,304,591 | 12/1981 | Mueller et al. | 424/484 X |
| 4,344,857 | 8/1982 | Shasha et al. | 252/316 |
| 4,349,553 | 9/1982 | Brown | 424/484 X |
| 4,375,535 | 3/1983 | Kightlinger et al. | 424/285 X |
| 4,400,391 | 8/1983 | Connick, Jr. | 71/88 |
| 4,401,456 | 8/1983 | Connick, Jr. | 424/488 X |
| 4,421,759 | 12/1983 | Boisvenue | 424/405 X |
| 4,436,719 | 3/1984 | Lindaberry | 424/407 |
| 4,497,930 | 2/1985 | Yamasaki et al. | 524/556 |
| 4,500,338 | 2/1985 | Young et al. | 424/484 X |
| 4,639,366 | 1/1987 | Heller | 424/484 |
| 4,640,044 | 2/1987 | Varnon | 424/405 X |
| 4,663,341 | 5/1987 | Jacobson | 514/256 X |
| 4,663,346 | 5/1987 | Coulston et al. | 514/456 |
| 4,667,436 | 5/1987 | Benson | 424/405 X |
| 4,677,003 | 6/1987 | Redlich et al. | 71/3 X |
| 4,681,806 | 7/1987 | Matkan et al. | 71/3 X |
| 4,707,359 | 11/1987 | McMullen | 71/3 X |
| 4,722,838 | 2/1988 | Tocker | 424/405 X |
| 4,743,448 | 5/1988 | Bahadir et al. | 424/405 |
| 4,818,534 | 4/1989 | Levy | 424/405 X |
| 4,818,536 | 4/1989 | Meyers et al. | 424/409 |

FOREIGN PATENT DOCUMENTS 2108517 5/1983 United Kingdom .
2141023 12/1984 United Kingdom .

Primary Examiner—Thurman K. Page
Attorney, Agent, or Firm—Finnegan, Henderson, Farabow, Garrett & Dunner

[57] ABSTRACT

Superabsorbent solid organic polymers which absorb over 100 times their weight in water are used in flowable, aquatic environment insect population control compositions of varying viscosities. Methods for using the superabsorbent polymer insecticidal delivery agents for the control of aquatic environment insect populations, including mosquito population control methods, in an area needing aquatic environment insect population control treatment, or in a dry area that is expected to need aquatic environment insect population control, are described.

11 Claims, No Drawings

OTHER PUBLICATIONS

*The Insecticide, Herbicide, Fungicide Quick Guide*, B. G. Page et al., Thomson Publications, 1987.
*Insect Control Guide*, Florida Agricultural Extension Service, Institute of Food and Agricultural Sciences University of Florida, Gainsville.
*Agricultural Chemicals*, Book I, "Insecticides, Acaricides and Ovicides", W. T. Thomas, 1985–1986, Revision, Thomson Publications.
*Agricultural Chemicals* Book II, "Herbicides", W. T. Thomson, 1986–1987, Revision, Thomson Publications.
*Agricultural Chemicals* Book III, "Fumigants, Growth Regulators, Repellents, and Rodenticides", W. T. Thomson, 1986, Revision, Thomson Publications.
*CRC Handbook of Natural Pesticides*, vol. III, "Insect Growth Regulators", Parts A and B, E. David Morgan, et al, CRC Press, Including an Introduction and Index Portion.
*Freshwater Vegetation Management*, Edward O. Gangstad, Thomas Publications, 1986.
*Flies of Public Health Importance*, CDC Training Guide, Insect Control Series, U.S. Department of Health, Education and Welfare, H. G. Scott et al., Apr. 1958.
*Guidelines for the Control of Insect and Mite Pests of Foods, Fibers, Feeds, Ornamentals, Livestock, and Households*, U.S. Department of Agriculture, Agricultural Research Service, Agriculture Handbook No. 584, Jan. 1982.
*Scientific Guide to Pest Control Operations*, Second Edition (Revised), L. C. Truman et al, Purdue University, 1967.
*Aquatic and Wetland Plants of Florida*, D. P. Tarver et al., Bureau of Aquatic Plant Research and Control, Florida Department of Natural Resources, 1978.
*Complete Guide to Pest Control–With and Without Chemicals*, G. W. Ware, Thomas Publications, 1980.
*Herbicide Handbook* of the Weed Science Society of America, Fifth Edition 1983.
*Technical Bulletin* Relating to "Sonar ®", Herbicide, Elan Co Products Company.

*Technical Bulletin* Relating to "Scout TM", Herbicide for Broad Spectrum Aquatic Weed Control, Monsanto Company.
*Technical Bulletin* Relating to "System L", and "System E", Aquatic Herbicides, 4-D Products, Inc.
*Technical Bulletin* Relating to "Agricultural Intermediates", Emulsifiers, Spray Adjuvants, Surfactants, Dispersants, Polymers for Agricultural Applications, Rohm Haas Company.
*Technical Bulletin*, Relating to "Terra-Sorb", Including MSDS on Terra-Sorb, Terra-Sorb AG, GB, HB and 200G.
*Product Bulletin,* Relating to "Sanwet®", Including MSDS on Sanwet IM-1500, 1500P, 1500F and 1000.
Culigel TM SP Superabsorbent Polymer Label and Research and Development Update: Culigel TM SP Superabsorbent Polymer.
*Technical Bulletin* Relating to "Hydrothol® 191," Granular Aquatic Algaecide and Herbicide, Pennwalt.
*Technical Bulletin* Relating to "Komeen®", Aquatic Herbicide, Sandoz, Inc.
*Technical Bulletin* Relating to "K-Tea" Algaecide, Cocide Chemical Corporation.
*Technical Bulletin* Relating to "Morwet® EFW Powder", Surfactant, DeSoto, Inc.
*Technical Bulletin* Relating to "Poly Control 2", Sticker and Drift Control Agent for Pesticides, JLB International, Inc.
*Technical Bulletin* Relating to "Rhodia 2,4-D Gran 20" Herbicide, Rhone-Poulenc Chemical Company.
*Technical Bulletin* Relating to "Revenge TM," Systemic Herbicide, Hopkins Agricultural Company.
*Technical Bulletin* Relating to "Banvel® 720" Herbicide, Velsicol Chemical Corp.
*Technical Bulletin,* "Chem-trol TM," Spray Additive Deposition and Drift Retardant, Loveland Industries, Inc.
*Product Bulletin* Relating to "Ortho Diquat Herbicide-H/A". Chevron Chemical Company.
*Technical Bulletin* Relating to "Dissolvo TM -45", A Water Soluble, Heat Sealable, Stable Pouching Material, Gilbreth International Corp.
*Technical Bulletin* Relating to "Fenoxycarb", Insect Growth Regulator, Maag.
*Technical Bulletin* Relating to "Ferro-Tech" Agglomeration Equipment, Ferro-Tech.
*Technical Bulletin* Relating to "Hydout TM" Aquatic Weed Killer, Pennwalt Corp.
*Technical Bulletin,* Relating to "Cytrol® Amitrole-T," Liquid Weed Killer.
*Technical Bulletin,* Relating to "Aquathol® K", Aquatic Herbicide.
*Technical Bulletin,* Relating to "Casoron®, G-10" Herbicide, Aquatic Weed Control.
*Technical Bulletin* Relating to "Cutrine®-Plus." Algaecide/Herbicide.
*Technical Bulletin* Relating to "A and V-70 Granular", Granulated Algaecide.
*Technical Bulletin* Relating to "Aquazine®" Algaecide, for Control of Algae and Certain Pond Weeds, Ciba-Geigy.
*Technical Bulletin* Relating to "Aquastore®" Soil Additive, Cyanamid. Including MSDS on Aquastore® 1, 2, 3 Soil Water Retention Aid and Aquastore Absorbent Polymer.
Material Safety Data Sheet, "Super Sorb", Super Absorbent Company, Inc.
*Technical Data* Relating to "Super Slurper" from U.S. Department of Agriculture.
*Technical Data* Relating to "Water Lock®," Including A-100 Series, G-100 Series, L-Series, B-200 Series, and J-500 Series.
*Technical Data,* Relating to "Aridall" Including 1080, 1078, 1091, 1092, and 1098.
*Technical Bulletin,* Relating to "Adjuvant List", State of Florida, Department of Natural Resources.
*Report* Relating to "Agrigel", Hazelton Raltech, Inc.
*Technical Bulletin,* Relating to "Aquashade", Aquatic Plant Growth Control.
*Technical Bulletin,* Relating to "Amine 6D" Herbicide, Asgrow Florida Company.
Levy et al., "Effect of Water Quality on the Efficacy of Water-Base Suspensions of Arosurf® MSF Against Larvae of *Aedes Taeiorhynchus:* Bioassay Evaluations," *Journal of the American Mosquito Control Association,* vol. 3, No. 6, pp. 631-641, Dec. 1987.
Roorda et al., "Zero-Order Release of Oxprenolol-HCl, A New Approach", *Journal of Controlled Release,* 7 (1988) 45-52.
Kamal et al., "Uptake of $^{14}$C-Simetryn by Duckweed (lemna minor) During Release from a Polymer Matrix and the Consequent Herbicidal Effects", *Journal of Controlled Release,* 7 (1988) 39-44.
Wing et al., "Amylose Content of Starch Controls the Release of Encapsulated Bioactive Agents", *Journal of Controlled Release,* 7 (1988) 33-37.
Trimnell et al., "Autoencapsulation: A New Method for Entrapping Pesticides Within Starch", *Journal of Controlled Release,* 7 (1988) 25-31.
*Modern Mosquito Control,* 5th Addition, Cyanamid.
Proceedings of the 14th International Symposium on Controlled Release of Bioactive Materials (1987), Controlled Release Society, Inc., Selected Proceedings Including pp. 158-167, 202-210, 244-252, 284-292 and 310, including a copy of the Table of Contents.
Program and Abstracts of 15th International Symposium on Controlled Release of Bioactive Materials, held in Basel, Switzerland, Aug. 15-19, 1988, Including Paper Nos. 15, 17, 19, 20, 23, 27, 30, 31, 55, 110, 130, 135, 139, 152, 170, 171, 173, 175, 190, 191, 195, 201, 204 and 262.
Levy et al., "Control of Immature Mosquitoes With a Single-, Joint-, or Multi-Action Polymer-Base Insecticide Delivery System," presented at the 15th International Symposium on Controlled Release of Bioactive Materials held in Basel, Switzerland, Aug. 15-19, 1988.
Levy et al., "Control of Immature Mosquitoes With a Single-, Joint-, or Multi-Action Polymer-base Insecticide Delivery System," presented at the 18th International Congress of Entomology, University of British Columbia, Vancouver, BC, Canada, Jul. 3-9, 1988.
"Super Slurper", Mar. 1988, *Popular Science,* p. 9, Article Discloses the Use of Nematodes in Combination with Super Slurper for use on Citrus Roots before Plant to Control Weevils.

Hester, "Field Phytotoxicity Studies with Arosurf® MSF", Department of Health and Rehabilitative Services, West Florida Arthropod Research Laboratory.
Axtell et al., "Encapsulation of the Mosquito Fungal Pathogen *Lagenidium Giganteum* (Oomycetes:-Lagenidiales) in Calcium Alginate," *Journal of the American Mosquito Control Association*, vol. 3, No. 3, pp. 450–459, Sep. 1987.
O'Neill, "Membrane Systems", *Controlled Release Technologies*, Chapter 4, pp. 129–182.
Kydonieus, "Other Controlled Release Technologies and Application", *Controlled Release Technologies*, Chapter 13, pp. 235–257.
Thomson, "A Guide to Agricultural Spray Adjuvants Used in the United States", 1986 Edition, including a Copy of Table of Contents and Selected pp. 50, 105, 107, 109, 111, 112, 154 and 155.
Levy et al., "Experimental Joint Action Formulations of Arosurf® MSF and *Bacillus Thuringiensis* Var. *Israelensis* or *Bacillus Sphaericus*", presented at 1987 AMCA Meeting Seattle, Washington, Mar. 29–Apr. 2.
Levy et al., "Laboratory Evaluations of Experimental Formulations of Arosurf® MSF and *Bacillus Thuringiensis* Var. *Israelensis, Bacillus Sphaericus* or Abate® 4–E" presented at 1987 FAMA Meeting Palm Beach, Florida, May 31–Jun. 3.
Morrill, *Journal of the American Mosquito Control Association,* News and Notes, pp. 565–566, vol. 2, No. 4, Dec. 1986, cites a Newsweek Article giving a brief mention to the possibility of "Microsponges" for the Release of Insect Repellents, including copy of Table of Contents.
Miller, "Dimensionally Stable Soluble Pouches for Safety", Pesticide Formulations and Application System, vol. 8, American Society for Testing and Materials, 1988.
*FRASS Newsletter,* vol. 8, No. 1, 1985, discloses a Starch Graft Polymer (SGP) called "Super Slurper" for Use in Coating Seeds, Preventing Soil Erosion, Fighting Fires, and Absorbing Chemical Spills.
"Arosurf® MSF, "Mosquito Larvicide and Pupicide, Technical Bulletin on this product as a Mosquito Control Treatment.
*Technical Bulletin,* "Teknar®," Larvicide for Mosquito and Blackfly Control prepared from *Bacillus Thuringiensis* berliner, var. *israelensis.*
*Technical Bulletin,* "Vectobac-G®," Granular Formulation of *Bacillus Thuringiensis* formulated as Granules with a Carrier of Corn Cob Particles.
"Pyrenone®, Tossits®," Encapsulated Larvicide.
"Bactimos Briquet," A Sustained Release Mosquito Control Product.
Baines, "Biodegradation of Polyvinyl Alcohol" and Bryan et al., Bioeegradation of Synthetic Warp Sizes.
Technical Bulletin, Water Soluble Films, including "Quick Sol A and P," Edisol-m, EM-1100, QSA 2000 and Mono-Sol.
Leppla, "Gelling Agents for Insect Diet: From Mush to Medium", Discussion of Natural Thickeners and their Chemical Structures.
"Altosid® Briquet, Product Application Bulletin", Technical Bulletin, No. 1115–81–2, Zoecon Corporation, Formulation designed to Time Release Insect Growth Regulator.
*Material Safety Data Sheet,* Grain Processing Corporation, Water Lock® Superabsorbent Polymer "G" Series.
*Data Sheet,* Super Absorbent Company, "Super Sorb".
*Material Safety Data Sheet* "Terra-Sorb".
*Material Safety Data Sheet* "Terra-Sorb GB".
*Product Data Sheet,* "Water Lock G-100 Superabsorbent Polymer", Grain Processing Corporation.
SGP®, "Safety of SGP® 502S Absorbent Polymer", Material Published from General Mills Chemical Inc.
Prichard et al., "Super Soil Moisturizer Challenges Others in Growing Industry" *Ornamentals South,* edited from a Speech to the American Institute of Landscape Architects, Las Vegas, Nevada, Aug. 22, 1981.
Del Deterling, "Super Slurper Gets Your Crop Moving Earlier", *Progressive Farmer,* Feb. 1981.
Weaver et al., "A Practical Process for the Preparation of Super Slurper, a Starch Based Polymer With a Large Capacity to Absorb Water", *Die Starke 29. Jahrg. 1977/Nr. 12, S.413–422.*
"Super Slurper: Compound with a Super Thirst", Reprinted from *Agricultural Research,* Jun. 1975, Published by the U.S. Department of Agriculture.
Whitmore, "Transplant Survival Improved", *Christmas Trees,* vol. 10, No. 1, Jan. 1982.
Burgess et al., "A New Method for Applying Arosurf® MSF (Monomolecular Surface Film Formulations)", *Journal of American Mosquito Control Association,* vol. 1, No. 2, pp. 245–247, Jun. 1985.
Levy et al., "Effect of Low Temperature on the Mosquito Larvicide and Pupicide Arosurf® MSF (Monomolecular Surface Film) and Adol® 85 (Indicator Oil): Physical Evaluations", *Mosquito News,* vol. 44, No. 3, pp. 419–422, Sep. 1984.
Levy et al., "Florida Mosquito Control Districts Use Arosurf® 66–E2", *Pest Control,* Field Guide, Apr., 1983.
Levy et al., "Comparative Efficacy of Technical and Water-Base Formulations of Arosurf® MSF Against *Aedes Taeniarhynchus*", *Journal of American Mosquito Control Association,* vol. 2, No. 4, pp. 560–562, Dec. 1986.
Levy et al., "Laboratory Evaluations of Formulations of Arosurf® MSF and *Bacillus Sphaericus* Against Larvae and Pupae of *Culex Quinguefasciatus*", *Journal of American Mosquito Control Association,* vol. 2, No. 2, pp. 233–236, Jun. 1986.
Levy et al., "Control of Immature Mosquitoes Through Applied Surface Chemistry", *Proceedings of the Florida Anti-Mosquito Association,* vol. 51, No. 2, pp. 68–71.
Levy et al., "Investigations on the Mosquito Control Potential of Formulations of Arosurf® MSF and Conventional Larvicides", *Mosquito News,* vol. 44, No. 4, pp. 592–595, Dec. 1984.

Levy et al., "Efficacy of Arosurf® MSF (Monomolecular Surface Film) Base Formulations of *Bacillus Thuringiensis* var. *Israelensis* Against the Mixed Populations of Mosquito Larvae and Pupae: Bioassay and Preliminary Field Evaluations", *Mosquito News*, vol. 44, No. 4, pp. 537–543, Dec. 1984.

Levy et al., "Additional Studies on the Use of the Monomolecular Surface Film Arosurf® 66-E2 for Operational Control of Mosquito Larvae and Pupae", *Journal of Florida Anti-Mosquito Association*, vol. 53, No. 2, pp. 100–106, 1982.

Hertlein et al., "An Injection Method for Spraying Biological Control Agents and a Monomolecular Surface Film for Control of Immature Mosquitoes", *Journal of American Mosquito Control Association*, vol. 1, No. 2, pp. 255–257, Jun. 1985.

Levy et al., "Efficacy of the Organic Surface Film Isostearyl Alcohol Containing Two Oxyethylene Groups for Control of Culex and Psorophora Mosquitoes: Laboratory and Field Studies", *Mosquito News*, vol. 42, No. 1, pp. 1–11, Mar. 1982.

Levy et al., "Control of Larvae and Pupae of *Anpoheles Quadrimaculatus* and *Anopheles crucians* in Natural Paludal Ponds With The Monomolecular Surface Film Isostearyl Alcohol Containing Two Oxyethylene Groups", *Mosquito News*, Vol. 42, No. 2, pp. 172–178, Jun. 1982.

Levy et al., "Ground and Aerial Application of a Monomolecular Organic Surface Film to Control Salt-Marsh Mosquitoes in Natural Habitats of Southwestern Florida", *Mosquito News*, vol. 41, No. 2, pp. 291–301, Jun. 1981.

Levy et al., "Persistence of the Mosquito Larvicide and Pupicide Arosurf® MSF in Permanent and Semi-Permanent Habitats", *Journal of Florida Anti-Mosquito Association*, vol. 56, No. 1, pp. 32–36, 1985.

Levy et al., "Formulations for Enhancing the Mosquito Larvicidal Action and Persistence of the Monomolecular Surface Film Isostearyl Alcohol Containing Two Oxyethylene Groups (Aro-surf® MSF)", *Journal of Florida Anti-Mosquito Association*, vol. 55, No. 1, pp. 31–34, 1984.

Harwood et al., Entomology in Human and Animal Health, Seventh Edition, 1979, Macmillan Publishing Co., Inc., New York, N.Y., Title page and Table of Contents.

Agis F. Kyeonieus, *Controlled Release Technologies: Method, Theory, and Applications*, vols. I and II, 1980, CRC Press, Inc., Boco Raton, Fla., and Specifically pp. 1 through 19 and 116 through 127 of vol. I, which relate to Information on Controlled Release in General and Specifically to Herbicides; pp. 240 through 246 of vol. I, which relate to Controlled Release from Ultramicroporous Triacetate; vol. II, pp. 241 through 257, which Relate to Controlled Release from Gels including a list of Cited Patent Literature; and pp. 8 through 62 of vol. II, which relate to the Biodegradative Controlled Release of Pesticides from Polymeric Substances, as well as a copy of the Detailed Table of Contents.

Richard Baker, *Controlled Release Technologies of Biologically Active Agents*, 1987, John Wiley & Sons, New York, N.Y., pp. 177–191, as well as the detailed Table of Contents.

Levy et al., "Control of Immature Mosquitoes With Liquid and Solid Formulations of a Monomolecular Organic Surface Film", presented at the Joint Meeting of the American Mosquito Control Association and California Mosquito and Vector Control Association, Apr. 18–22, 1982, Sacramento, Calif., pp. 106–108.

FLOWABLE INSECTICIDAL DELIVERY COMPOSITIONS AND METHODS FOR CONTROLLING INSECT POPULATIONS IN AN AQUATIC ENVIRONMENT

CROSS-REFERENCE TO RELATED APPLICATION

This is a continuation-in-part of my application entitled "Improved Insecticidal Compositions and Methods for Controlling a Population of Insects in an Aquatic Environment", Ser. No. 032,532, filed Apr. 1, 1987 and now U.S. Pat. No. 4,818,534.

BACKGROUND AND SUMMARY OF THE INVENTION

1. Field of the Invention

The present invention relates to a variable-viscosity, insecticidal delivery formulation composed of a liquid carrier, e.g., water or oil, and one or more solid superabsorbent polymers with one or more liquid or solid insecticidal or noninsecticidal film-forming or surface-active agents, ovicides, larvicides, pupicides, insecticides, biological control agents, pathogens, parasites, microbial control agents, insect growth regulators, conventional toxicants, pesticides, or chemosterilants, with or without herbicides or attractants, repellents, pheromones, alcohols, diluents, or other additives. The present invention also relates to a method of applying the insecticidal delivery composition with one or more active insecticidal ingredients, with or without one or more herbicides or other additives, as variable-viscosity sprays or sols to an aquatic environment having a natural population of aquatic environment insects, for the purpose of controlling that population of insects. The present invention also relates to the use of the insecticidal delivery composition for a pretreatment application to an aquatic insect dry habitat in order to control that population of aquatic insects that will breed when the insect habitat becomes flooded by rain or tides. This invention further relates to a facile method of combining two or more active insecticidal ingredients in a liquid carrier, e.g., water or oil, with one or more film-forming agents, and one or more superabsorbent polymers, with or without one or more herbicides or other additives, to formulate variable-viscosity insecticidal delivery compositions that are flowable (i.e., sprayable, pumpable, or injectable) for ground or aerial application. The application of superabsorbent polymers makes possible the mixing of active insecticidal and herbicidal ingredients that would otherwise be difficult or substantially impossible to mix homogeneously in a liquid carrier, e.g., water or oil, as joint- or multiple-action formulations for spray application. Furthermore, this invention relates to the use of one or more superabsorbent polymers in the formulation of a variety of sprayable/flowable insecticide compositions to synergize, enhance, activate, carry, disperse, release, stabilize, bind, couple, encapsulate, agglomerate, regulate, thicken, suspend, preserve, protect, etc., one or more of the active and/or inactive formulation components in the flowable formulation and/or in the target aquatic, semi-aquatic, or pretreatment environment(s) in which the formulation is applied, in a manner that will provide improved flowable formulations, more efficient formulating (mixing) procedures, more efficient application, and/or generally improve the insecticidal efficacy (performance) of the resultant formulation against the target organism(s).

2. General Background

In particular, the present invention is directed against mosquitoes that breed in permanent or semipermanent, natural or artificial, aquatic habitats. Mosquitoes of major importance to be controlled by the present invention are species of the genera of Aedes, Anopheles, Culex, Culiseta, Coquillettidia, Deinocerites, Mansonia, Orthopodomyia, Psorophora, Uranotaenia and Wyeomyia. It is the main objective of this invention to direct the use of the flowable insecticidal delivery compositions(s) for the control of the immature aquatic states of various species of mosquitoes before they become biting adults capable of being a nuisance and/or transmitting a disease. This technique is cost-effective and reduces the environmental and health hazards that can result when insecticides are extensively broadcast over large areas for the control of the adult stages.

In addition to mosquitoes, other species of aquatic environment insects such as biting and nonbiting midges, black flies, moth flies, crane flies, horse flies, deer flies, hover or flower flies can constitute a nuisance and often a health threat to humans and livestock. Thus, their growth as a population, if unchecked, can be detrimental. The medical and veterinary importance of various species of mosquitoes and other important aquatic environment insects are discussed in detail by Robert F. Harwood and Maurice T. James in, *Entomology In Human and Animal Health*, Seventh Edition, 1979, MacMillan Publishing Co., Inc., New York, N.Y., which is incorporated herein by reference. Therefore, the scope of the present invention also relates to the use of the flowable insecticidal delivery composition with one or more active insecticidal ingredients, with or without one or more herbicides or other additives, for controlling various species of aquatic environment insects other than mosquitoes.

Various compositions and methods for controlling and killing insects are well known. A number of patents discuss the use of pesticides or insecticides. U.S. Pat. No. 3,535,423 discloses a wettable powder pesticide concentrate that may be dispersed in water. This is described as allowing the otherwise insoluble pesticide to become soluble in water. U.S. Pat. No. 4,267,280 discloses controlled release pesticides and their preparation. These pesticides are described as polymers with a macro-molecular backbone and pendant groups having pesticidal groups chemically linked thereto and prepared by reacting a pesticide having a replaceable hydrogen with a multifunctional isocyanate to form an adduct which is then reacted with a polyol polymer substrate. U.S. Pat. Nos. 4,400,391 and 4,401,456 disclose the use of alginate gel beads to encapsulate bioactive materials to provide for their controlled release. The patents describe beads being made to either float or sink and they may contain insecticides. These beads are also described as acting as carriers to place the bioactive material near the target species, for example, a floating bead containing a herbicide releasing the herbicide in close proximity to floating aquatic weeds or the beads falling through foliage to release a herbicide into the soil. U.S. Pat. No. 4,344,857 contains a disclosure that is similar to those immediately above; however, it involves encapsulation by xanthate derivatives and does not disclose the ability to be used in conjunction with an aqueous environment.

A number of patents describe the use of substances other than pesticides to control the growth of insects. U.S. Pat. No. 4,053,627 discloses a controlled release system for juvenile hormones in aqueous environments. This is described as being accomplished with alginate gel discs comprising alginate, a solubilizing agent, and a salt which yields cations, and containing the juvenile hormone. U.S. Pat. No. 4,160,033 discloses a method for the control of mosquitoes by the use of film-forming materials. The method is disclosed as involving the use of a film of organic material which reduces the surface tension of the body of water, and subsequently causes the mosquito larvae and pupae to drown.

At the present time, ground and aerial application of non-petroleum film-forming agents such as Arosurf® MSF for mosquito control is performed mainly by spraying the technical liquid or vigorously agitated suspensions of the film-forming agent and water. However, technical film-forming agent(s) such as Arosurf® MSF applied as conventional liquid sprays are usually adversely effected by wind drift and cannot penetrate dense vegetation at the low recommended application rates. Therefore, most of the costly insecticidal film-forming agent impinges on the vegetation and does not reach the water where the mosquitoes are breeding and/or is translocated by the wind to areas not intended for application. In addition, the use of water as a diluent for application of large volumes for easier vegetative penetration without overdosing requires frequent high-speed/high-shear agitation or the use of high-pressure/-high-shear, water-injection systems to adequately suspend the film-forming agent in the water for accurate application rates. Mosquitocidal film-forming agents such as Arosurf® MSF are virtually insoluble in water, and therefore require continuous or frequently repeated high-shear agitation to effectively suspend or resuspend the Arosurf® MSF in the water carrier.

The aqueous absorbency mechanism of acrylic-based superabsorbent polymers has been described by the Chemdal Corporation (Arlington Heights, Ill. 60004) in their Technical Data Sheets on Aridall® Superabsorbent Polymers. The absorbency of acrylic-based superabsorbent polymers is due to carboxylic groups located on the backbone of the superabsorbent polymer. When water contacts the superabsorbent polymer, these groups solvate rapidly and develop mutually repulsive negative charges. This causes the superabsorbent polymer to uncoil and absorb many times its weight in water. Crosslinking prevents solution of the superabsorbent polymer. The aqueous medium rapidly becomes oriented on the surface of the superabsorbent polymer by virtue of hydrogen bonding. The resulting gel has remarkable ability to hold the aqueous medium even under pressure. Superabsorbent polymers hold fluids by a physiochemical mechanism.

None of the prior art methods or compositions for controlling insect populations are without disadvantages. One major problem associated with many of the aforementioned compositions and methods of the prior art is their inability to simultaneously apply immiscible, or otherwise incompatible substances to the area to be treated. It has been found that while film-forming materials, when combined with water and ovicides, larvicides, pupicides, insecticides, pesticides, conventional toxicants, biological control agents, microbial control agents, pathogens, parasites, chemosterilants, or insect growth regulators, with or without herbicides or diluents such as attractants, repellents, pheromones, alcohols, etc., may produce improved insect controlling efficacy over single active component formulations, problems with mixing the ingredients homogeneously often result. For example, blends of Arosurf® MSF (a film-forming agent) and water or technical and/or water-base blends or Arosurf® MSF and various formulations of *Bacillus thuringiensis* var. israelensis (*B.t.i.*), or *Bacillus sphaericus* or Abate® 4-E do not form homogeneous and stable suspensions when casually mixed, and therefore require frequent and vigorous agitation. When allowed to stand, the components would separate into distinct layers because of the differences in their respective specific gravities, and/or the presence of incompatible active and/or inert formulation ingredients, and therefore, these joint- or multiple-action formulations would require continuous agitation and/or reagitation to effectively remix the components just prior to their application. (See Levy et al. 1984, *Mosquito News* 4:537–543; Levy et al. 1986. *Journal of the American Mosquito Control Association* 2:233–236.) These mixing and remixing requirements make it very difficult to apply these liquid (aqueous) formulations by conventional means.

While it may be possible to incorporate some known insecticidal components, singly, jointly or multiply as aqueous- or oil-base sprays, these formulations cannot regulate (retard) the release rate of active insecticidal components, and lack the ability to control both mosquito larvae and pupae simultaneously while effectively and spontaneously spreading the active ingredients over the target aquatic habitat.

Since other flowable insecticidal compositions do not have rapid self-spreading characteristics, they require even applications to assure that there is effective control of the target aquatic insects that may be widely dispersed in the aquatic habitat. In addition, the other flowable insecticidal components usually affect only one immature developmental stage. However, the use of insecticidal delivery compositions made with one or more superabsorbent polymers of the present invention with, for example, a pupicidal film-forming agent (e.g., Arosurf® MSF), a larvicidal agent such at *B.t.i.* or *Bacillus sphaericus*, and water, have self-spreading potential and can kill mosquito larvae, pupae, or emerging adults rapidly in areas far removed from the initial points of application, significantly better than either of the active formulation components. These formulations can also kill floating eggs and egg rafts of certain species of mosquitoes and also entrap and drown females that oviposit on the surface of the water. Although Arosurf® MSF can kill mosquito larvae and pupae, its impact on larval populations is usually very slow and requires higher application rates than for pupal control.

No single-, joint-, or multiple-action flowable, water-compatible formulations are available that claim rapid larvicidal and pupicidal action with some degree of ovicidal and adulticidal action, self-spreading characteristics, and field persistence. For example, commercial mosquitocidal preparations of *Bacillus thuringiensis* var. israelensis formulated for water-base spray applications (e.g., Vectobac® -AS, Vectobac® -12AS; Teknar®, Teknar® HP-D, Teknar® WDC; Bactimos® Wettable Powder; Skeetal®F), *Bacillus sphaericus* (BSP-1), Abate® 4-E, Dursban®, Baytex® 4 and Baytex® LC, Furadan®, Baygon® 70% wettable powder, Dimilin® wettable powder, Altosid® Liquid Larvicide are available that have slow or quick immature stage kill potential; however, these do not have rapid multi-developmental stage control potential, do not have self-spreading characteristics, are typically composed of only one active insecticidal ingredient that cannot be simply and rapidly detected or monitored under field conditions by insecticide applicators, and are not formulated with superabsorbent polymers.

Attempts have been made to incorporate film-forming agents such as those described in U.S. Pat. No. 4,160,033 with a variety of conventional insecticides in water (See Levy et al. 1984, *Mosquito News:* 44 pp. 537-543, pp. 592–595; Levy et al. 1986, *Journal American Mosquito Control Association* 2:233–236). However, these attempts have been unsuccessful because the film-forming agent (i.e., Arosurf® MSF) would readily separate into layers even after vigorous agitation due to incompatibilities of the film-forming agent with water or other insecticides and/or inert ingredients in the formulation. Therefore, the resultant formulations could not be homogeneously mixed to assure that accurate application rates of the active components would be applied in the field against the target aquatic pest.

Specific Objects

It is therefore an object of the present invention to provide flowable, aqueous- or oil-base superabsorbent polymer compositions and methods for the pretreated dry habitat control and aquatic control of a population of aquatic environment insects, particularly mosquitoes, which overcome the problems and deficiencies of the prior art.

It is also an object of the present invention to provide flowable, aqueous- or oil-base superabsorbent polymer compositions and methods which are easy to prepare (formulate) and use (apply), and which are erodible (biodegradable) and safe to the environment, but which is effective for use in controlling one, but preferably more than one immature stage of a natural population of aquatic environment insects, particularly mosquitoes.

It is further an object of the present invention to provide superabsorbent polymer compositions and methods which can incorporate a wide variety of ingredients into a single flowable, aqueous- or oil-base insecticidal delivery formulation to control a broad spectrum of aquatic environment insect populations, particularly mosquitoes, and to provide for the variable time-release of those ingredients.

These and other objects are accomplished by the compositions and methods of the present invention.

Specific Aspects

In accordance with one aspect of the present invention, there is provided flowable, aqueous- or oil- base insecticidal delivery compositions for controlling a population of aquatic environment insects, the flowable delivery compositions being applied as a pretreatment before the target habitat is flooded or as a direct treatment to the aquatic habitat. The composition includes at least one superabsorbent polymer, and at least one insecticidal agent, alone or in combination with a diluent or surface-active agent, the superabsorbent polymer and insecticidal agent being present in a total amount effective to control the population of aquatic environment insects. The superabsorbent polymer(s) being present at a concentration adapted to allow satisfactory mixing of the formulation components and release modification of the insecticidal agent(s) from the flowable formulation.

In accordance with another aspect of the present invention, there is provided flowable, aqueous- or oil-base insecticidal delivery compositions for controlling a population of aquatic environment insects which includes at least one superabsorbent polymer, and at least one different insecticidal agent which is a film-forming agent, the superabsorbent polymer and agent being present in a total amount effective to control the population of aquatic environment insects, the delivery compositions being applied as a variable-viscosity pretreatment application before the target habitat is flooded or as a direct treatment to the aquatic habitat.

In accordance with yet another aspect of the present invention, there is provided flowable, aqueous- or oil-base insecticidal delivery compositions for controlling a population of aquatic environment insects which includes at least one superabsorbent polymer, at least one different insecticidal agent which is a film-forming agent, and at least one additional compound. The additional compound is selected from larvicides; pupicides; ovicides; insecticides; toxicants; pesticides; biological control agents; microbial control agents; pathogens; parasites; insect growth regulators; chemosterilants; and mixtures thereof, with or without herbicides; attractants; pheromones; repellents; diluents; alcohols; surface-active agents; etc. The superabsorbent polymer, agent and additional compound are present in a total amount effective to control the population of aquatic environment insects, the flowable, variable-viscosity aqueous- or oil-base delivery compositions being applied as a pretreatment before the target habitat is flooded or as a direct treatment to the aquatic habitat.

In accordance with another aspect of the present invention, there is provided a method for controlling a population of aquatic environment insects which includes the steps of:

preparing flowable, variable-viscosity aqueous- or oil-base insecticidal delivery compositions which includes at least one superabsorbent polymer and at least one insecticidal agent which includes a film-forming agent, by a series of variable time/speed blending, and/or salt/electrolyte conditioning treatments;

applying said flowable, aqueous- or oil-base insecticidal delivery compositions in an amount effective to control the population of aquatic environment insects, to an aquatic area needing aquatic insect control treatment, the flowable, aqueous- or oil-base delivery compositions being applied as a pretreatment before the target habitat is flooded or as a direct treatment to the aquatic habitat.

In accordance with still another aspect of the present invention, there is provided a method for controlling a population of aquatic insects. The method includes the steps of:

preparing flowable, variable-viscosity aqueous- or oil-base insecticidal delivery compositions which includes at least one superabsorbent polymer and a least one insecticidal agent which includes a film-forming agent and at least one additional compound. The additional compound is selected from ovicides; larvicides; pupicides; insecticides; conventional toxicants; pesticides; biological control agents; microbial control agents; pathogens; parasites; insect growth regulators; chemosterilants; and mixtures thereof, with or without herbicides; attractants; repellents; pheromones; diluents; alcohols; surface-active agents; etc.; and applying said flowable, aqueous- or oil-base insecticidal delivery compositions in an amount effective to control the population of aquatic environment insects, to an aquatic environment needing aquatic insect control treatment before the target habitat is flooded or as a direct treatment to the aquatic habitat.

The superabsorbent polymers of the present invention are synthetic organic polymers which are solid and hydrophilic absorbing over 100 times their weight in water. Generally, these superabsorbent polymers are chosen from acrylamide and acrylate polymers, copolymers and ter-polymers. These polymers can be suitably crosslinked and/or modified. These superabsorbent polymers are typically in a power, flake, or granular form, adapted to optimize the compatibility and/or release rates of insecticidal components in water or oil and, thereby, enhance the activity of flowable insecticidal formulations against the target aquatic insect.

The acrylamide and acrylate superabsorbent polymers may be, for example, acrylamide alkali metal or alkali metal/aluminum acrylate co-polymers; propenenitrile homo-polymers, hydrolyzed, alkali metal or alkali metal/aluminum salts; polymers of propenamide and propenoic acid, alkali metal salts; hydrolyzed acrylonitrile co-polymers, and starch graft co-polymers and ter-polymers thereof. All of these are designed to be hydrophilic, absorbing over 100 times their weight in water.

The present invention has been found to be particularly effective in controlling natural populations of mosquito species such as *Aedes taeniorhynchus, Aedes sollicitans, Anopheles atropos,* and *Culex nigripalpus* that can breed in brackish/salt water habitats. The use of the invention to control species of fresh or polluted water mosquitoes such as *Aedes aegypti, Aedes albopictus, Aedes triseriatus, Anopheles quadrimaculatus, Anopheles crucians, Culex quinquefasciatus, Psorophora columbiae, Psorophora ciliata, Wyeomyia mitchellii, Wyeomyia vanduzeei,* etc., in semipermanent or permanent aquatic environment areas needing mosquito control treatment is also proposed.

Specific Advantages

The present invention provides numerous advantages over prior compositions and methods to control the population of aquatic environment insects such as mosquitoes. For example, the flowable, aqueous- or oil-base superabsorbent polymer formulations of the present invention may be composed of one or more of a wide choice of either nontoxic or toxic biological or microbial control agents, pathogens, parasites, insect growth regulators, monomolecular surface films, larvicides, ovicides, pupicides, insecticides, chemosterilants, pesticides, and/or toxicants, with or without herbicides or attractants, repellents, pheromones, diluents, alcohols, etc., depending on the type or nature of the habitat to be controlled, the environmental impact, and/or the type of aquatic developmental stage or insect species to be controlled. The superabsorbent polymer formulations of the present invention are flowable (i.e., sprayable, pumpable or injectable) and are mainly based on water; however, these formulations can also be based on oil. The flowable, aqueous- or oil-base superabsorbent polymer formulations of the present invention are biodegradable. They are also storage stable, basically as stable as the individual components; however, increased stability may occur from encapsulation of the active components within the aqueous- or oil-base formulation. Aqueous- or oil-base formulations of the present invention can be of varying viscosities which may be required for a particular application. The flowable formulations of the present invention can have some variable time-release, either quick, or gradual, depending on the concentration and types of superabsorbent polymers in the aqueous- or oil-base formulation. The present invention provides a suspending/compatibility agent to assure homogeneous delivery of joint- or multiple-active, aqueous- or oil-base formulations of otherwise incompatible soluble or insoluble liquid or powdered insecticidal and/or non-insecticidal agents without the necessity of continuous or repetitive high-speed/high-shear agitation for effective spray application of the active components. Flowable, variable-viscosity aqueous- or oil-base formulations of the present invention can be used as a pretreatment application to areas that are dry but are known to breed when flooded, thereby assuring that the first broods will be controlled. Also, encapsulation of the active insecticidal agents within the variable-viscosity, flowable superabsorbent polymer formulation can protect the active components from degradation or decomposition from ultra-violet radiation, microbial action, temperature effects, run-off, etc., when the formulation is applied as a pretreatment application. The present invention is also not restricted to applications to any one type of aquatic environment.

Other objects, aspects and advantages of the present invention will be apparent to one of ordinary skill in the art from the following:

DESCRIPTION OF THE PREFERRED EMBODIMENTS

Surprisingly, it has been found that certain superabsorbent polymers constitute a novel class of chemicals useful in flowable, aqueous- or oil-base insecticidal delivery compositions for controlling the population of insects in an aquatic environment area needing aquatic environment insect control treatment.

A flowable insecticidal delivery composition is any composition which can carry, or be adapted to carry, insecticidal agent(s), biologically active or biologically inactive agent(s), etc., to the target habitat, natural or artificial, aquatic or dry. In a preferred embodiment, the flowable insecticidal delivery agent is a mixture of one or more superabsorbent polymers and water or oil. Superabsorbent polymers, including starch graft co-polymers, are well known in the art. See, for example, those described in U.S. Pat. Nos. 4,375,535 and 4,497,930 (incorporated herein by reference) which have had uses as adhesives, flocculants, sizes, water-retaining materials for agriculture and water-absorbing materials for sanitary materials. However, the advantages attendant the use of superabsorbent polymers in a flowable, aqueous- or oil-base insecticidal delivery composition and more specifically for mosquito control in an aquatic environment, have gone completely unrecognized.

The superabsorbent polymers of the present invention are synthetic organic polymers which are solid and hydrophilic, absorbing over 100 times their weight in water. These superabsorbent polymers are substantially water-insoluble, and are typically in a powder, flake, or granular form, adapted to optimize the compatibility or release rates of insecticidal components in water and thereby, enhance the activity or efficacy of the aqueous- or oil-base insecticidal formulations against the target aquatic insect.

Generally, these superabsorbent polymers are chosen from acrylamide and acrylate polymers, co-polymers and ter-polymers, which may optionally be modified by cross-linking or grafting with, e.g., starch.

The acrylamide and acrylate superabsorbent polymers may be, for example, acrylamide alkali metal or alkali metal/aluminum acrylate co-polymers; propenenitrile homo-polymers, hydrolyzed, alkali metal or alkali metal/aluminum salts; hydrolyzed acrylonitrile co-polymers, and starch graft co-polymers and ter-polymers thereof. All of these are designed to be hydrophilic, absorbing over 100 times their weight in water. The resulting hydrophilic polymers can absorb from over one hundred to greater than about 5,000, more typically around 500 to about 1,000, times their own weight in water (measured using distilled water, pH 7.5, 25° C., 760 mm Hg., absorption within about 30 seconds). However, the water absorption or swelling capacity and rates typically vary with each specific superabsorbent polymer.

One class of superabsorbent polymers include combinations of a starch and organic monomers, oligomers, polymers, co-polymers, or ter-polymers. They may be manufactured in a variety of ways, for example, the methods described in U.S. Pat. Nos. 4,375,535 and 4,497,930, and can be, for example, the product of grafting corn starch (amylopectin) with acrylonitrile (an acrylic monomer or oligomer).

The superabsorbent polymers can also be acrylics, propenoic or acrylonitrile/acrylamide-base polymers or co-polymers or ter-polymers that also show superabsorbency properties such as cross-linked or cross-linked modified polymers.

It has also been observed that superabsorbent polymers alone, or mixed in water with one or more insecticidal agent(s), have the ability to further swell in water, thereby altering the rates of release of the substance(s) in the formulation. Superabsorbent polymers also have the ability under certain conditions to reform or contract to a crystal or congealed-like consistency similar to their original form when evaporation has caused the water to be removed from the sol or gel-like formulation and then swell or re-gel when additional water is added. This ability to be functional after repetitive periods of wetting and drying is advantageous for pretreatment applications, applications to habitats that experience rapid flooding and drying cycles, and/or for prolonging the release of active components. In addition, insecticides encapsulated in the variable-viscosity sol, gel-like, or crystal or congealed-like formulations can be protected from climatological and biological degradation in pretreatment and/or in semipermanent habitats; thereby prolonging their field activity. Storage or shelf life may also be prolonged in several of these formulations.

Non-limiting specific examples of superabsorbent polymers with differential swelling properties, and which are particularly useful as insecticidal delivery agents include:

(1) a co-polymer of acrylamide sodium acrylate (Terra-Sorb GB);

(2) hydrolyzed starch-polyacrylonitrile (Terra-Sorb);

(3) 2-propenenitrile, homo-polymer, hydrolyzed, sodium salt or poly (acrylamide-co-sodium acrylate) or poly (2-propenamide-co-2-propenoic acid, sodium salt), (Water Lock® Superabsorbent Polymer G-100);

(4) starch-g-poly (2-propenamide-co-2-propenoic acid, sodium salt), (Water Lock® Superabsorbent polymer A-100);

(5) starch-g-poly (2-propenamide-co-2-propenoic acid), (Water Lock® Superabsorbent Polymer A-200);

(6) starch-g-poly (2-propenamide-co-2 -propenoic acid, potassium salt), (Water Lock® Superabsorbent Polymer B-204);

(7) starch-g-poly (2-propenamide-co-2-propenoic acid, mixed sodium and aluminum salt), (Water Lock® Superabsorbent Polymer A-222);

(8) poly (2-propenamide-co-2-propenoic acid, sodium salt), (Water Lock® Superabsorbent polymer G-400);

(9) poly-2-propenoic acid, sodium salt (Water Lock® Superabsorbent Polymer J-500 or Aqua Keep® J-500);

(10) sodium polyacrylate superabsorbent polymers (Aqua Keep® J-400 and J-550);

(11) starch-g-poly (acrylonitrile) or starch-g-poly (acrylamide-co-sodium acrylate), (General Mills SGP® 5025);

(12) starch acrylonitrile co-polymer (Super Sorb/AG Sorbent);

(13) cross-linked modified polyacrylamides (Aquastore® and Aquastore® F); and

(14) cross-linked acrylics (Aridall® 1078, 1080, 1091, 1125, 1092, or 1098).

Superabsorbent polymers are generally nontoxic, biodegradable, and relatively inexpensive to buy or produce. See, for example, U.S. Pat. Nos. 3,661,815 and 4,159,260, which are incorporated herein by reference.

An insecticidal agent of the present invention is a compound which is effective in an aqueous- or oil-base superabsorbent polymer formulation in controlling a population of aquatic environment insects in an aquatic area needing aquatic insect control treatment. In a preferred embodiment, insecticidal agents include film-forming agents, ovicides, larvicides, pupicides, pesticides, insecticides, toxicants, chemosterilants, biological control agents, pathogens, parasites, microbial control agents, and insect growth regulators. These insecticidal agents can be used alone or in combination; however, in a more preferred embodiment, the insecticidal agent contains at least one film-forming agent. Insecticidal agents can also be formulated with herbicides, attractants, repellents, pheromones, or other diluents that enhance the action of the formulations but show insufficient insecticidal activity.

Electrolytes/salts interfere somewhat with the hydrogen bonding. Crosslinked acrylic-based superabsorbent polymers always absorb less aqueous medium when electrolytes/salts are present. Normally, the addition of water or water-based insecticidal formulations to various concentrations of superabsorbent polymers, or visa versa, can form sols or gels of various consistencies (viscosities) or stiffnesses that may or may not be flowable. However, high-shear mixing or the addition of various salts/electrolytes can break or interfere with the gel structure or the hydrogen bonding, thereby producing flowable (sprayable) superabsorbent polymer/insecticide aqueous formulations that have the desired viscosity. Viscosity modification will mainly be a function of the active and/or inactive formulation components, the water absorption characteristics of the superabsorbent polymer (i.e., the type and amount of superabsorbent polymers), shear time and strength used to mix the formulation, and/or the concentration and type of salts/electrolytes used to modify the sol or gel consistency of the formulation. Therefore, the viscosity of the aqueous formulation containing one or more superabsorbent polymers can be altered to achieve optimum flowability, droplet size and quantity, and thereby improve the general ground or aerial application characteristics of the formulation for maximum control of the target aquatic insect. Furthermore, active insecticidal ingredients encapsulated in the viscous/semi-viscous but flowable, aqueous (or oil base) superabsorbent polymer formulation can be protected from degradation from the effects of ultra-violet radiation, volatilization, temperature, microbial activity, evaporation, run-off, etc., particularly when used in pretreatment habitats. Furthermore, evaporation of water from the flowable, aqueous superabsorbent/pesticide formulation can result in a solid congealed-like pesticide encapsulated matrix (as described in U.S. patent application Ser. No. 032,532, the substance of which is incorporated herein by reference), thereby protecting the active components for prolonged periods until release of the insecticidal ingredient is triggered when the preaquatic (pretreatment) habitat is flooded with water.

Film-forming agents that are mosquitocidal are generally water-immiscible organic chemicals which form a monomolecular or duplex films on water. The chemicals are generally nonionic, nonvolatile and water immiscible liquids. They may have a low freezing point, a boiling point above the maximum air temperature of the environment into which they are placed, and are capable of rapid and spontaneous spreading with high respreading potentials.

Examples of liquid, semisolid, or solid film-forming or surface-active agents useful in conjunction with the present invention for insecticidal and/or noninsecticidal purposes are: the organic chemicals described in U.S. Pat. No. 4,160,033, which is herein incorporated by reference; and organic chemicals that reduce the water surface tension to greater than 31 dynes/cm and/or have an HLB No. greater than 10. Film-forming agents such as 1-propanol, tridecyl alcohol, 2-ethyl butanol, 2-ethyl hexanol, 1-hexanol, acetone, xylene, decyl alcohol, polyoxyethylene (20) sorbitan trioleate, polyoxyethylene alkyl aryl ether, polyoxyethylene (5) sorbitan monooleate, isostearyl alcohol containing 20 oxyethylene groups, sorbitan monooleate, isostearyl alcohol containing 10 oxyethylene groups, Morwet ® surfactants, cetyl alcohol, stearyl alcohol, etc., may be useful.

HLB stands for "Hydrophile-Lipophile Balance," as defined in THE ATLAS HLB SYSTEM, Atlas Chemical Industries, Inc. (4th printing), 1963. The HLB number is an indication of the percentage of the hydrophilic portion of the nonionic emulsifier molecule, as defined on pages 3 and 18 of this reference.

A pupicide is any material that can kill that specific developmental stage of certain aquatic insects called a pupa. Pupicides are usually chemicals that kill pupae directly by forming petroleum or nonpetroleum films on the surface of water that cause the pupae to drown. This stage is nonfeeding and directly precedes the adult stage. Examples of pupicides useful in accordance with the present invention are Arosurf ® MSF or other film-forming agents described in U.S. Pat. No. 4,160,033. Biological/microbial pupae control agents such as bacteria, fungi, protozoa, viruses, rickettsiae or nematodes may also be used at a future time.

Formulations of at least one film-forming agent such as Arosurf ® MSF with superabsorbent polymer(s) and water of the present invention into a variable-viscosity, flowable formulation allows a significantly more homogeneous and stable (persistent) suspension of Arosurf ® MSF and water to form after an initial high shear mixing, as well as larger droplets of the aqueous formulation to penetrate through the vegetative canopy for release of the active film-forming agent into the target aquatic habitat with significantly less wind drift-related problems. In this manner, the need for repeated high-shear mixing/remixing is virtually eliminated. Also, premixed formulations of superabsorbent polymer(s), Arosurf ® MSF, and water can be stored as aqueous formulations for direct use for ground or aerial application with little or no additional mixing. In addition, flowable, variable-viscosity formulations of superabsorbent polymer(s), a film-forming agent(s) such as Arosurf ® MSF and water of the present invention can effect a mechanism for slowing down the rate of release of active ingredients, thereby extending the field life or persistence of the mosquito-controlling surface film for a greater period of time than would be expected with conventional technical or agitated non-superabsorbent polymer aqueous formulations of Arosurf ® MSF.

The rate of release and/or re-release of the mosquitocidal film-forming agent from the variable-viscosity, flowable superabsorbent polymer formulation will be mainly dependent on the viscosity of the formulation, that is, the ratio of superabsorbent polymer to water (or oil), the water absorbing (swelling) characteristics of the superabsorbent polymers(s), the water quality of the natural or artificial habitat and/or formulation diluent, and on the climatological moisture/water conditions to which the formulation is exposed. High-shear mixing/agitation techniques, the addition of various concentrations of salts/electrolytes (e.g., NaCl, KCl, etc.) to the superabsorbent polymer/pesticide mixture, and/or the use of invert oil techniques are proposed for regulating the viscosity of the flowable superabsorbent polymer formulations.

The proposed variable-viscosity, film-forming agent/superabsorbent polymer(s), flowable, aqueous formulations will resist wind drift (i.e., have greater drift retardant characteristics than simple aqueous spray formulations having no superabsorbent polymer(s)), and initially show a differential ability to float and/or sink depending on the specific gravity of the superabsorbent polymer(s). The addition of various concentrations of one or more superabsorbent polymer(s) can also enhance the mixing capability and stability (i.e., reduce or eliminate product(s) separation or stratification) of one or more active and/or inactive formulation components (e.g., formulations of Arosurf ® MSF and *Bacillus thuringiensis* var. israelensis (B.t.i.) or *Bacillus sphaericus* (*B. sphaericus*) in a water base; see Levy et al. 1984, *Mosquito News*, 44:537–543 and Levy et al. 1986, *Journal of the American Mosquito Control Association*, 2:233–236) in water by acting as a compatibility or suspending agent.

A larvicide is any material that can kill that specific developmental stage of certain aquatic insects called a larva. Larvicides can kill larvae after ingestion of a toxic material, kill on or after contact with the integument, or kill by physical (nontoxic) and/or toxic mean by causing the larvae to drown. The larval stage is a feeding stage that usually has several molting or growth phases called instars. For example, in mosquitoes there are four larval instars. The larval stage directly precedes the pupal stage. Examples of larvicides useful in accordance with the present invention include biological control agents or microbial control agents such as *Bacillus thuringiensis* var. israelensis (e.g., Vectobac ®, Bactimos ®, Teknar ®, Skeetal ®, Mosquito Attack ®) or *Bacillus sphaericus* (e.g., BSP-1); conventional toxicants such as Abate ®, Baytex ®, Dursban ®, Prentox ®, Pyrenone ®, resmethrin, malathion, pyrethrins, allethrin, Baygon ®, Furadan ®, methoxychlor, etc; and nonpetroleum film-forming oils such as Arosurf ® MSF. Fungi (such as *Lacenidium giganteum*, mycelia and oospores), protozoa, viruses, rickettsiae and nematodes may also be used.

Insect growth regulators (IGRs) are chemicals such as juvenile hormone or anti-juvenile hormone analogues that kill the target aquatic environment insect in one or more immature stages by adversely affecting the molting or developmental cycle. IGRs are not considered to be direct larvicides or pupicides. For the most part, larvae that are exposed to the chemical continue to develop normally until they reach the pupal stage where they die. Examples of IGRs are Altosid®, Dimilin®, and fenoxycarb (Pictyl®).

Insecticides (i.e., pupicides, larvicides, insect growth regulators, pathogens, etc., useful in the present invention are discussed in W. T. Thomas, 1985, *Agricultural Chemicals, Book* 1 *Insecticides,* 1985–86 Revision, Thomas Publications, Fresno, Calif., pp. 1–255, and in George O. Poinar, Jr. and Gerald M. Thomas, 1978, *Diagnostic Manual for the Identification of Insect Pathogens,* Plenum Press, New York, pp. 1–218.

The use of one or more herbicidal ingredients in the flowable, superabsorbent polymer insecticidal compositions is proposed for selected ground or aerial applications. It has been shown that certain aquatic weeds (plants) can provide excellent breeding grounds for disease carrying mosquitoes, and programs aimed at the control of algae and submersed, floating, or emergent plants and/or marginal aquatic plants have been shown to reduce the incidence of various mosquito-transmitted diseases (Dr. Edward O. Gangstad, 1986, *Freshwater Vegetation Management,* Thomas Publications, Fresno, Calif., 377 pp.). For example, aquatic weeds such as coontail, widgeon grass, waterweed, pondweed, stonewort, bladderwort and filamentous green algae (particularly Spirogyra) have been shown to enhance the development of several species of Anopheles mosquitoes that can be vectors of malaria in the United States and overseas. In addition, *Culex tarsalis,* a vector of St. Louis and Western encephalitis in the midwestern and western United States, breed in aquatic plant (weed)-choaked irrigation and drainage ditches, seeps, and roadside impoundments. Also, larvae and pupae of mosquitoes of the genera Mansonia and Coquillettidia (potential vectors of Eastern encephalitis) derive their oxygen by puncture from air trapped in hollow aquatic plant stems. In addition, *Aedes aegypti,* a vector of dengue and yellow fever can breed inside certain water plants. Therefore, the use of herbicides to complement the insecticidal action of the superabsorbent polymers formulations of the present invention is proposed to enhance general mosquito control operations in areas containing significant densities of aquatic plants.

Herbicidal materials proposed for use in the present invention can include one or more materials from the groups, phenoxy compounds; benzoic, acetic acids and phthalic compound; dinitro anilines, nitrites, amides, acetamides and anilides; carbamates; heterocyclic nitrogen derivatives; urea compounds; metal organics and inorganics; petroleum derivatives; phosphates; carbothiolates; cyclic compounds; halogenated hydrocarbons; dinitros; aliphatic acids; and others. Various herbicidal formulations in these groups are discussed in detail in W. T. Thomson, 1986, *Agricultural Chemicals, Book II, Herbicides,* 1986–87 Revision, Thomson Publications, Fresno, Calif., 301 pp. and in Dr. Edward O. Gangstad, 1986, *Freshwater Vegetation Management,* Thomas Publications, Fresno, Calif., 377 pp. Herbicides and mixtures thereof of specific interest in these groups used for controlling floating weeds, immersed broadleaf weeds, submersed weeds, algae, irrigation and drainage ditch bank weeds, and irrigation and drainage canal weeds, include Acrolein® ammonium sulfamate, Aquazine®, Banvel®, Casoron®, copper, copper sulfate, Cutrine®, Dalapon®, Dichlone®, Diquat®, Endothal®, Fenac®, Karmex®, Monuron®, petroleum solvents, Rodeo®, Roundup®, Simazine®, Sonar®, Spike®, 2,4-D, Velpar®, and xylene.

Insect population is used here to refer to one or more group(s) or species of aquatic environment insects that breed in any type of aquatic environment or habitat requiring control treatment. The population as used herein denotes a natural or artificial breeding area and the like or the aquatic insects, pupae, larvae and eggs contained within any geographical area needing aquatic environment insect control treatment. For example, a field, yard, pasture, pot hole, salt marsh, ditch, tire, woods, lake, stream, river, bay, pond, etc., may be treated. Of course, the area needing aquatic environment insect control treatment can be any size and the present invention is only limited by the amount of time, equipment, and material available.

One or more superabsorbent polymers can be used to form flowable, variable-viscosity single-, joint-, or multi-purpose, aqueous- or oil-base formulations composed of one or more insecticides, etc., with or without herbicides or other diluents, solvents, surfactants, attractants, etc., for spray applications by conventional ground or aerial techniques, to control a variety of aquatic insects in a variety of aquatic or preaquatic (pretreatment) habitats. The superabsorbent polymers are used in a variety of flowable, aqueous- or oil-base insecticide formulations to synergize, enhance, activate, carry, release, stabilize, bind, agglomerate, regulate, thicken, suspend, neutralize, preserve, etc., one or more of the active and/or inactive formulation components in the flowable formulation and/or in the target aquatic environment(s) in which the formulation is applied, in a manner that will provide improved formulations, and more efficient formulation application.

Variable-viscosity, aqueous- or oil-base formulations are flowable and have the ability to release one or more active agents when applied to aquatic environments. The rate of release is dependent on the concentration of formulation components (e.g., superabsorbent polymers, water or oil), the swelling characteristics of the superabsorbent polymer(s), and on the habitat or climatological condition to which the formulation is exposed or released (e.g., dry or wet, pretreatment or aquatic).

Variable-viscosity, superabsorbent polymer-based formulations can be formulated by admixing an active agent with one or more superabsorbent polymer(s) and water or oil in any suitable order and then treating said formulation with vigorous or high-shear mixing and/or electrolytes/salts. The ratio of superabsorbent polymer(s) to water or oil depends on the desired viscosity, the nature of the superabsorbent polymer(s) and the method used to render it flowable. The ratio of superabsorbent polymer(s) to water is suitably 0.001:100 to 1:1. The amount of active agent in the flowable formulation is generally 0.00001 to 50 weight percent, preferably 0.0001 to 25 weight percent.

One technique used to render a viscous/semi-viscous aqueous superabsorbent polymer composition flowable is suitably vigorous or high-shear mixing/agitation. Any suitable equipment or technique used to incorporate insecticides into an aqueous emulsion can be suitably used to render a non-flowable superabsorbent-base formulation flowable. Invert oil techniques are also appropriate for mixing and dispensing a highly viscous aqueous superabsorbent polymer formulation composed of an insecticide and surface-active agent, with or without herbicides or other additives.

Normally, unmixed formulations of superabsorbent polymers and water have a tendency to form gels of such a high viscosity that they are not flowable. An additional technique used to render a viscous superabsorbent polymer composition of the present invention flowable, is the additional of varying concentrations of one or more salt(s)/electrolyte(s) such as sodium chloride. However any suitable salt/electrolyte such as potassium chloride, magnesium chloride, calcium chloride, sodium sulfite, etc., can be employed. These salts/electrolytes have a tendency to interfere with the hydrogen bonding or reduce the hydrophilic bonding of the water to the gel. Also, superabsorbent polymers (e.g., crosslinked acrylics) absorb less water when electrolytes are present. This technique can be used by itself or in conjunction with vigorous or high-shear mixing to produce a flowable (i.e., sprayable, pumpable or injectable) aqueous superabsorbent polymer formulation having an active ingredient such as an insecticide, pesticide or other suitable agents. The technique and degree of viscosity variation are dependent upon the active and inactive ingredients in the superabsorbent polymer formulation. Relevant factors in the degree of viscosity of the formulations are the water swelling characteristics of the superabsorbent polymer (i.e., the type and amount of polymer), water concentration and quality used in the formulation, the shear time and strength used to mix or agitate the formulation, and/or the type and concentration of salts/electrolytes used to modify the gel consistency. Using a suitable combination of viscosity-varying techniques, the aqueous formulation can be altered to obtain optimum characteristics such as flowability (sprayability), encapsulation of active ingredients, droplet size variations, substrate adherence, slower release rates of active components, and wind drift retardation.

It is contemplated that aqueous insecticidal delivery formulations made flowable by vigorous or high-shear agitation and/or the addition of salts/electrolytes can be used to control immature stages of mosquitoes. The superabsorbent polymer(s) used in the flowable aqueous formulation effectively suspends or assists in the mixing of the various active and inactive ingredients, regardless of their compatibility with each other and/or the aqueous medium, to form a homogeneous formulation. For example, Super Sorb, Arosurf® MSF and Water, or Super Sorb, Arosurf® MSF, water and *B.t.i.* or *B. sphaericus,* can be effectively blended together to form a flowable composition with sufficient high-shear agitation and/or salt/electrolyte addition such that the ingredients will not separate or partition for an extended period of time. In contrast, under normal circumstances such ingredients would rapidly separate requiring repetitive high-shear agitation to render the composition suitably homogeneous for application purposes. As such, large quantities of the formulation can be prepared sufficiently ahead of time and suitably stored until needed, when they can then be applied by conventional spray techniques, without the cumbersome need for repetitive vigorous or high-shear reagitation.

The flowable aqueous compositions also are advantageous when used in aerial applications in their ability to resist wind drift. By altering viscosity significantly, droplet density, size, shape and surface characteristics can be altered to significantly affect the droplet wind resistance, flow, and deposition characteristics when applied with an aerial delivery system. Additionally, aquatic buoyancy characteristics can be suitably altered in the flowable formulation such as by varying the type and concentration of superabsorbent polymers having different specific gravities, incorporating micro bubbles in the shearing technique, or using high molecular weight additives for the sinking formulations. The variable-viscosity composition also can be suitably modified to effect its surface characteristics with oils, wetting agents, surface-active agents, and the like. Varying concentrations of superabsorbent polymers replaced with surface-active agents can be incorporated such as to effect the adhesiveness of the water-base spray formulation causing it to cling or adhere to desired strata or plants when delivered to the target pretreatment environment. Other formulation additives can include the above surfactants as well as suitable polymeric agents such as plasticizers, water-soluble polymers, film-forming polymers, etc.

The concentration of superabsorbent polymer(s) in the aqueous- or oil-base formulations of the present invention has been shown to effect the release rates of the active insecticidal ingredients. In addition, varying the ratio of different types of these superabsorbent polymers of the present invention that have differential water uptake characteristics (e.g., Water Lock® and Aridall® products) in a single formulation may effect a mechanism to further enhance slow-release characteristics of certain active insecticidal ingredients. In addition, the varying specific gravities (i.e., less than or greater than one) of the superabsorbent polymers and active insecticidal ingredients of the present invention can be used to develop flowable formulations that initially float and/or sink for use in a variety of habitats to optimize the kill of a variety of aquatic insect species.

It should be noted that certain electrolytes/salts (e.g., alkali metal halides such as NaCl) have been shown to interfere with hydrogen bonding of the superabsorbent polymers in an aqueous medium. Also, crosslinked acrylic superabsorbent polymers have been shown to absorb less water when electrolytes are present. This can have an impact on the swelling and population control ability of the flowable, insecticidal delivery composition (e.g., the release rate of certain insecticidal agents that are formulated there within). Therefore, it is possible to utilize certain electrolytes/salts in superabsorbent polymer-base formulations as another mechanism to alter (enhance in this case) or adjust the release rate of various active ingredients incorporated in these formulations. The salt/electrolyte content of the aquatic habitat may also have an effect on kill of the target species such as mosquitoes by affecting the superabsorbent polymer swelling, breakdown/decomposition of viscous formulations, and/or release of active insecticidal ingredients encapsulated within the flowable, aqueous superabsorbent polymer formulations.

The following ar examples of comparative bioassays that demonstrate effective control of larvae, pupae, and/or emerging adults of a variety of mosquito species with single- and joint-action, flowable aqueous formulations of a superabsorbent polymer and one or more insect control agents. Examples demonstrating formulation viscosity modification with high mixing and/or electrolyte/salt conditioning and slow release are also presented. All parts, percentages and ratios are by weight unless otherwise noted.

EXAMPLES I-VII

Data was collected from the use of aqueous insecticidal delivery formulations composed of Super Sorb, Water Lock ®, Aqua Keep ®, and/or Aridall ® superabsorbent polymers and film-forming agent isostearyl alcohol containing two oxyethylene groups (Arosurf ® MSF); and a superabsorbent polymer, Arosurf ® MSF and B.t.i., or *B. sphaericus;* with or without high-shear and salt/electrolyte conditioning. Arosurf ® MSF is the only film-forming agent (so-called monomolecular surface film) that is presently registered by the Environmental Protection Agency (E.P.A.) for use as a mosquito larvicide and pupicide and licensed under U.S. Pat. No. 4,160,033. *B.t.i.* products have E.P.A. registration while *B. sphaericus* (BSP-1) has an E.P.A. experimental use permit pending E.P.A. registration.

Mixing compatibility/viscosity modification evaluations were conducted with high-shear mixing or salt-/electrolyte conditioning with formulations of Water Lock ®, Aqua Keep ®, Super Sorb, Aridall ®, and/or Aquastore ® F superabsorbent polymers, Arosurf ® MSF, and water; and a superabsorbent polymer, Arosurf ® MSF, *B.t.i.* or *B. sphaericus,* and water or oil; or a superabsorbent polymer, Arosurf ® MSF, 2,4-D, and water; as well as with 50/50 superabsorbent polymer blends. Although similar mixing compatibilities were obtained, the results indicated that salt/electrolyte type and the concentration, and the shear time/strength would vary depending on the superabsorbency of the polymer(s) and the type of insecticide and/or herbicide in the aqueous formulation. Mosquito bioassays indicated that the larvicidal and pupicidal efficacy were generally equivalent.

Film-forming agents such as sorbitan monooleate, oleyl alcohol, 75% sorbitan monooleate and 25% 2-ethyl butanol or 2-propanol, oleyl alcohol containing 2 oxyethylene groups, and lauryl ether containing 4 oxyethylene groups were also evaluated as substitutes for Arosurf ® MSF. These materials were formulated in water with Super Sorb or Water Lock ® G-100 to determine mixing compatibility and viscosity modification only. Although these materials were not evaluated against larvae and pupae, mixing studies indicated that homogeneous formulations were obtained, thereby suggesting that comparable mosquito-controlling efficacy would result. In addition, the insect growth regulators Altosid ® Liquid Larvicide and fenoxycarb were also formulated with water, Arosurf ® MSF and Super Sorb or Water Lock ® G-100, to determine formulation compatibilities. Results indicate that joint-action formulations of these materials can also be utilized.

Various concentrations of salts/electrolytes such as sodium chloride, potassium chloride, magnesium chloride, calcium chloride, or sodium sulfite were used in combination with mild mixing (not high-speed/high-shear) to determine the optimum conditions for viscosity modification and component compatibility of aqueous formulations of Arosurf ® MSF, and a Super Sorb, Water Lock ®, Aqua Keep ®, or Aridall ® superabsorbent polymer, with or without *B.t.i.* or *B. sphaericus.*

Results indicated that several types of variable-viscosity, superabsorbent polymer compositions of one or more insecticides and water were homogeneous, stable, and flowable could be formulated by varying the electrolyte(s)/salt(s) concentration and type.

In general, the data indicates that liquid film-forming or surface-active agents can be initially mixed with a superabsorbent polymer, alone, or in combination with water or oil, or one or more liquid or solid mosquito larvicides, ovicides, pupicides, insecticides, pesticides, biological control agents, microbial control agents, pathogens, parasites, conventional toxicants, and insect growth regulators, by high-speed or high-shear agitation, or salt/electrolyte conditioning procedures with mild agitation, to produce flowable, homogeneous and stable, single-, joint- or multiple-action, variable-viscosity aqueous- or oil-base formulations for single- and multi-stage mosquito control in the aquatic environment. Flowable formulations produced in this manner with one or more superabsorbent polymers can be premixed and stored for prolonged periods and will not require constant vigorous spray system agitation for effective field application of the aqueous- or oil-base suspensions/high-shear compositions.

Surprisingly, the data indicates that aqueous formulations of Super Sorb and Arosurf ® MSF generally produced faster control of larvae of *Aedes taeniorhynchus* than Arosurf ® MSF alone. The data suggests that the flowable, aqueous superabsorbent polymer formulations remained homogeneous and stable after initial mixing, and may produce an activation or larvicidal enhancement mechanism for Arosurf ® MSF against this mosquito species in the water qualities tested. It should be noted that the superabsorbent polymer alone showed no significant larvicidal activity. In general, some larvicidal enhancement was observed in tests against *Culex quinquefasciatus* with aqueous formulations of Super Sorb and Arosurf ® MSF. Tests against this species in fresh water showed initial larvicidal enhancement or comparable larvicidal efficacy over the test period when the superabsorbent polymer-/Arosurf ® MSF formulations were evaluated against Arosurf ® MSF alone (i.e., without polymer). It should be noted that larvae of the *Ae. taeniorhynchus* are significantly more sensitive to Arosurf ® MSF than *Cx. quinquefasciatus.* However, it should be noted that the salt marsh mosquito *Ae. taeniorhynchus* is the main pest mosquito in Lee County as well as in other coastal counties of Florida and other parts of the U.S.A.

EXAMPLE I

A flowable formulation was prepared in this example. Water, Arosurf ® MSF, and Super Sorb were mixed together in a glass beaker with a laboratory blender containing a shearing blade to produce an aqueous formulation that could be used to control mosquito larvae and pupae at application rates recommended for the control of immature mosquitoes. For example, 0.4 g of Super Sorb were added to 94.4 g of water purified by reverse osmosis filtration (RO) while mixing at 1800 rpm for 30 sec. Mixing speed was increased to 2400 rpm while adding 5.2 g of Arosurf ® MSF. Mixing was continued for 10 min. Observations indicated that the Arosurf ® MSF was homogeneously suspended in the water with the addition of 0.4% Super Sorb superabsorbent polymer to form a milky, semi-viscous flowable formulation. This formulation was easily sprayable from a plastic hand-pump sprayer. No visible stratification or separation of the formulation components was observed one hour after preparation. However, aqueous Arosurf® MSF formulations containing no Super Sorb and mixed in a similar manner began to separate into an Arosurf® MSF and a water phase within several minutes after blending. The non-superabsorbent polymer formulation had separated into 2 distinct phases 1 hour after mixing, and required reagitation/remixing to effectively resuspend the 2 components into a uniform mixture. The Super Sorb-base milky formulation appeared stable, i.e., the Arosurf® MSF and water did not appear to have separated, when observed at one, two, three and four week post-mixing intervals. Distinct separation of the Arosurf® MSF and water in the non-Super Sorb formulation was observed at each of these intervals, even though this formulation wa resuspended (remixed) after each weekly observation.

EXAMPLE II

Flowable formulations composed of 0.5–0.8% Super Sorb, Arosurf® MSF, B.t.i. (Bactimos® Primary Powder, Vectobac®-AS, or Teknar®) and reverse osmosis (RO) water or well water, as well as Super Sorb (0.5–0.8%), Arosurf® MSF, B. sphaericus (BSP-1), and RO or well water were prepared for application of active ingredients at rates recommended on the labels for control of larvae or pupae by blending techniques similar to those described in Example 1. The order of addition of the components, mixing speed (1200–4200 rpm), mixing intervals (start/stop), and mixing duration (15 sec–30 min) were dependent on the concentration of Super Sorb, concentration of Arosurf® MSF, water quality, and on the type, concentration and/or formulation of bacillus used in the aqueous composition. Results were similar to Example I, that is, observations indicated that homogeneous and persistent (non-separating) suspensions of the *B.t.i.* or *B. sphaericus* and Arosurf® MSF and water resulted at one, two, three, and four week post-mixing observation periods while non-superabsorbent polymer formulations of *B.t.i.* or *B. sphaericus* mixed with Arosurf® MSF and water separated into two or three distinct layers within 1 hr post-mixing. In fact, component partitioning began almost immediately after mixing. The duration and speed of mixing did not improve the compatibility or suspendability of one or more active ingredients in the non-superabsorbent polymer formulations.

EXAMPLE III

For an illustration of a flowable, oil-base formulation of the present invention, 310 g of Arosurf® MSF non-petroleum oil, 310 g of Aquastore® F polymer, and 10 g of *B.t.i.* (Vectobac® Technical Powder) were mixed in a beaker with a small electrically-powered mixer for ca. 10 min. When a drop of this semi-viscous, non-aqueous (i.e., oil base) flowable formulation was added to water with an eye dropper, a bead of gel formulation (specific gravity$>$1) instantly formed upon contact with the water and slowly expanded as the polymer absorbed water, thereby releasing both active agents (i.e., *B.t.i.* and Arosurf® MSF).

EXAMPLE IV

The comparative mosquito-controlling efficacy of the flowable, high-shear, aqueous formulation of Arosurf® MSF and Super Sorb superabsorbent polymer was determined in a series of bioassays against larvae and pupae of *Ae. taeniorhynchus* and *Cx. quinquefasciatus* in a variety of water qualities. Aqueous formulations were prepared in a manner similar to that described in Example I.

Bioassays were conducted in 400 ml glass beakers containing 250 ml of test water and 2nd to 4th instar larvae or combinations of 5 larvae and 5 pupae (3 replications/formulation). Aqueous formulations containing Super Sorb were allowed to sit unmixed for one hour post-blending and were not remixed, while aqueous formulations containing no Super Sorb were vigorously hand shaken for 1 minute prior to application. Flowable formulations were applied to the water surface with a glass pipette or microsyringe at application rates recommended for the control of mosquito larvae and pupae. Bioassays were conducted in a room maintained at 80° F. (ambient) and 80% RH.

Results of bioassays against larvae and pupae of *Ae. taeniorhynchus* and *Cx. quinquefasciatus* are presented in Table I. In general, the data indicated that the Arosurf® MSF aqueous formulations, containing varying amounts cf Super Sorb killed 2nd–4th instar larvae of *Ae. taeniorhynchus* as quick or faster than technical Arosurf® MSF and/or aqueous Arosurf® MSF containing no Super Sorb. Similar findings were recorded in bioassays against 2nd–4th instar larvae of *Cx. quinquefasciatus*; however, these were not as dramatic as the results obtained with larvae of *Ae. taeniorhynchus.*

Water quality of the formulation diluent and/or mosquito habitat, superabsorbent polymer concentration, and larval instar were shown to affect the rate of larvicidal action. Also, preliminary high-shear mixing results with Super Sorb, Aridall® 1092, Water Lock® G-100, or Aqua Keep® J-500 superabsorbent polymers and Arosurf® MSF, bacilli and water indicated that the type of polymer (i.e., the water absorbing characteristics) will affect the optimum percent concentration of superabsorbent polymer required for effective aqueous suspension of the formulation ingredients.

EXAMPLE V

As an alternative, or an addition to, vigorous or high-speed/high-shear mixing, to reduce viscosity and enhance the suspendability and/or mixing compatibility of one or more insecticidal or non-insecticidal components in an aqueous superabsorbent polymer-base formulation, additional viscosity/suspendability modification tests were conducted in 100 ml glass medicine bottles to determine if electrolytes/salts (e.g., 0.1–0.5%) such as sodium chloride, potassium chloride, magnesium chloride, calcium chloride or sodium sulfite could be used in combination with mild agitation (i.e., not high-shear) to decrease the viscosity (i.e., increase the flowability or fluidity) of variable-viscosity formulations (100 g total prepared) composed of reverse osmosis water, 5% Arosurf® MSF, and 0.5% of a superabsorbent polymer such as Aqua Keep® J-500, Super Sorb, or Aridall® 1092, with or without 5% *B.t.i.* (Vectobac® -AS) or 5% *B. sphaericus* (BSP-1), without adversely affecting the suspendability or mixing compatibility of the formulation components. Insecticidal ingredients were formulated for aqueous application to the water surface at 5.0 gal/acre at rates that were recommended on the labels for the control of mosquito larvae and pupae.

Results indicated that the salt/electrolyte concentration and type used in the aqueous formulation was dependent on the type (and concentration) of superabsorbent polymer and the type and concentration of insecticidal ingredients in the formulation. Also, the tests indicated that the order of adding the formulation components in water, as well as the type of salt/electrolyte used, could affect the ease of mixing, suspendability, or stability of the ingredients. In general, results suggested that stable, homogeneous formulations of water, Arosurf® MSF, a superabsorbent polymer, with or without a larvicidal bacillus, and an electrolyte/salt could be formed with mild agitation (i.e., hand-shaking). It should be noted that no separation, partitioning, or clumping of the components was observed at 24 hr post-mixing.

Comparative bioassays to determine the mosquito-controlling efficacy of hand-shaken (30 sec) aqueous formulations composed of 5.0% Vectobac® -AS or BSP-1 and 5.0% Arosurf® MSF and 0.5% Super Sorb or Aqua Keep® J-500 with 0.1% sodium chloride or sodium sulfite against 3rd–4th instar larvae and pupae of *Cx. quinquefasciatus* resulted in 100% mortality within 24–48 hr post-treatment. One hundred percent control of mixed larvae (3rd–4th instar) and pupae of *Ae. taeniorhynchus* was also observed in similar tests with the *B.t.i.* (Vectobac® -AS) formulation within 24 hr post-treatment. The same results were also recorded with the above compositions that were formulated with high-shear mixing but without a salt/electrolyte.

EXAMPLE VI

Additional mixing compatibility tests were conducted in 100 ml glass medicine bottles with compositions of 0.5 g Aqua Keep® J-500, Water Lock® A-100, or Aquastore®F, and 5 g Arosurf® MSF, 9.5 g 2,4-D, and 85 g R.O. water indicated that flowable, variable-viscosity superabsorbent polymer formulations composed of a mosquito larvicide/pupicide and a herbicide could be made with mild agitation (i.e., vigorous hand-shaking for 30 sec). No separate salts/electrolytes were added to the flowable formulation since the active ingredient in the E.P.A. registered herbicide formulation is 65.6% dimethylamine salt of 2,4-Dichlorophenoxyacetic acid. Flowable formulations were prepared for application of the active ingredients at label recommended rates, i.e., ca. 0.25 gal/acre Arosurf® MSF and 0.5 gal/acre 2,4-D, at 5.0 gal/acre total formulation. No clumping, stratification, or separation of the components in the flowable, superabsorbent polymer formulations were noted at 24 hr post-mixing, even though vigorous or high-shear agitation was not employed. Surface spreading activity of Arosurf® MSF was verified by the use of talc (see Example VII). Formulation viscosity varied with the type of superabsorbent polymer; however, all formulations were very flowable.

EXAMPLE VII

The slow release potential of an insecticidal ingredient from a variable-viscosity formulation of superabsorbent polymer was determined by laboratory spreading rate evaluations according to procedures established by Levy et al. 1984, *Mosquito News* 44:419–422. Super Sorb (2 g) and an R.O. water—10% Arosurf® MSF mixture (10 g) were blended with a high-shear dyna mixer. This aqueous formulation was applied to the water surface at one end of a stainless steel pan containing 7,570 ml of R.O. water that had been evenly dusted with 0.15 g baby powder-type talc at a formulation rate of ca. 0.53 g/pan or ca. 0.26 gal/acre Arosurf® MSF (3 replications). The spreading rates of Arosurf® MSF from the aqueous superabsorbent polymer formulation were compared to the spreading rates for technical Arosurf® MSF applied at 0.26 gal/acre. The comparative slow release potential of the formulation was determined by the average time in seconds needed for the formulation to move or translocate the powder to the opposite perimeter of the test pan. Results indicated that the floating, aqueous Super Sorb/Arosurf® MSF formulation translocated the powder to the perimeter of the pan in an average of 33.3 sec, while technical Arosurf® MSF translocated the powder in 5.3 sec; thereby indicating the slow release potential of Arosurf® from an aqueous superabsorbent polymer formulation.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

TABLE I

Efficacy of Superabsorbent polymer-base suspensions of Arosurf ® MSF and water against larvae and pupae of *Aedes taeniorhynchus* (A.T.) and *Culex quinquefasciatus* (C.Q.) as related to habitat and formulation water quality[1]

| Test no. | Species (habitat water quality) | Larval instar/ pupae(P) | Formulation[2] (% polymers) | Application rate per surface acre[3,4] | Cumulative percentage mortality of larvae, pupae and/or emerging adults at indicated posttreatment time period (days) 1 | 2 | 3 | 4 | 5 | 6 | 7 |
|---|---|---|---|---|---|---|---|---|---|---|---|
| 1a | A.T. (0% seawater) | 2nd | Polymers (0.35) + Arosurf MSF + R.O. water | 5.0 gal | 23.3 | 50 | 66.7 | 76.7 | 83.3 | 86.7 | 100 |
| | | | Arosurf MSF + well water | 5.0 gal | 36.7 | 46.7 | 63.3 | 83.3 | 90 | 90 | 100 |
| | | | Arosurf MSF | 0.26 gal | 16.7 | 36.7 | 63.3 | 70 | 83.3 | 86.7 | 100 |
| | | | Control | — | 0 | 0 | 3.3 | 3.3 | 3.3 | 3.3 | 3.3 |
| 1b | A.T. (6.25% seawater) | 2nd | Polymers (0.35) + Arosurf MSF + R.O. water | 5.0 gal | 70 | 100 | — | — | — | — | — |
| | | | Arosurf MSF + well water | 5.0 gal | 96.7 | 100 | — | — | — | — | — |
| | | | Arosurf MSF | 0.26 gal | 86.7 | 100 | — | — | — | — | — |
| | | | Control | — | 0 | 0 | — | — | — | — | — |
| 1c | A.T. (12.5% seawater | 2nd | Polymers (0.35) + Arosurf MSF + R.O. water | 5.0 gal | 100 | — | — | — | — | — | — |
| | | | Arosurf MSF + well water | 5.0 gal | 100 | — | — | — | — | — | — |
| | | | Arosurf MSF | 0.26 gal | 100 | — | — | — | — | — | — |
| | | | Control | — | 0 | — | — | — | — | — | — |
| 1d | A.T. (25% seawater) | 2nd | Polymers (0.35) + Arosurf MSF + R.O. water | 5.0 gal | 100 | — | — | — | — | — | — |
| | | | Arosurf MSF + well water | 5.0 gal | 100 | — | — | — | — | — | — |
| | | | Arosurf MSF | 0.26 gal | 100 | — | — | — | — | — | — |

TABLE I-continued

Efficacy of Superabsorbent polymer-base suspensions of Arosurf ® MSF and water against larvae and pupae of *Aedes taeniorhynchus* (A.T.) and *Culex quinquefasciatus* (C.Q.) as related to habitat and formulation water quality[1]

| Test no. | Species (habitat water quality) | Larval instar/ pupae(P) | Formulation[2] (% polymers) | Application rate per surface acre[3,4] | Cumulative percentage mortality of larvae, pupae and/or emerging adults at indicated posttreatment time period (days) | | | | | | |
|---|---|---|---|---|---|---|---|---|---|---|---|
| | | | | | 1 | 2 | 3 | 4 | 5 | 6 | 7 |
| 1e | A.T. (50% seawater) | 2nd | Control | — | 0 | — | — | — | — | — | — |
| | | | Polymers (0.35) + Arosurf MSF + R.O. water | 5.0 gal | 100 | — | — | — | — | — | — |
| | | | Arosurf MSF + well water | 5.0 gal | 100 | — | — | — | — | — | — |
| | | | Arosurf MSF | 0.26 gal | 100 | — | — | — | — | — | — |
| 1f | A.T. (75% seawater) | 2nd | Control | — | 0 | — | — | — | — | — | — |
| | | | Polymers (0.35) + Arosurf MSF + R.O. water | 5.0 gal | 100 | — | — | — | — | — | — |
| | | | Arosurf MSF + well water | 5.0 gal | 100 | — | — | — | — | — | — |
| | | | Arosurf MSF | 0.26 gal | 100 | — | — | — | — | — | — |
| 2a | A.T. (0% seawater) | 3rd | Control | — | 0 | — | — | — | — | — | — |
| | | | Polymers (0.5) + Arosurf MSF + well water | 5.0 gal | 16.7 | 23.3 | 50 | 63.3 | 90 | 100 | — |
| | | | Polymers (0.6) + Arosurf MSF + well water | 5.0 gal | 20 | 40 | 5.67 | 90 | 93.3 | 100 | — |
| | | | Arosurf MSF + well water | 5.0 gal | 16.7 | 46.7 | 46.7 | 63.3 | 83.3 | 100 | — |
| | | | Arosurf MSF | 0.26 gal | 23.3 | 23.3 | 43.3 | 70 | 83.3 | 100 | — |
| 2b | A.T. (50% seawater) | 3rd | Control | — | 0 | 0 | 3.3 | 3.3 | 3.3 | 3.3 | — |
| | | | Polymers (0.5) + Arosurf MSF + well water | 5.0 gal | 56.7 | 83.3 | 86.7 | 100 | — | — | — |
| | | | Polymers (0.6) + Arosurf MSF + well water | 5.0 gal | 73.3 | 93.3 | 96.7 | 100 | — | — | — |
| | | | Arosurf MSF + well water | 5.0 gal | 60 | 73.7 | 76.7 | 86.7 | 100 | — | — |
| | | | Arosurf MSF | 0.26 gal | 16.7 | 40 | 86.7 | 100 | — | — | — |
| 2c | A.T. (100% seawater) | 3rd | Control | — | 0 | 0 | 0 | 6.7 | 10 | — | — |
| | | | Polymers (0.5) + Arosurf MSF + well water | 5.0 gal | 100 | — | — | — | — | — | — |
| | | | Polymers (0.6) + Arosurf MSF + well water | 5.0 gal | 100 | — | — | — | — | — | — |
| | | | Arosurf MSF + well water | 5.0 gal | 93.3 | 93.3 | 96.7 | 100 | — | — | — |
| | | | Arosurf MSF | 0.26 gal | 53.3 | 76.7 | 80 | 83.3 | 96.7 | 100 | — |
| 3a | A.T. (6.25% seawater) | 4th | Control | — | 0 | 0 | 0 | 0 | 0 | 0 | — |
| | | | Polymers (0.35) + Arosurf MSF + R.O. water | 5.0 gal | 100 | — | — | — | — | — | — |
| | | | Arosurf MSF + well water | 5.0 gal | 96.7 | 100 | — | — | — | — | — |
| | | | Arosurf MSF | 0.26 gal | 90 | 93.3 | 100 | — | — | — | — |
| 3b | A.T. (12.5% seawater) | 4th | Control | — | 6.7 | 6.7 | 6.7 | — | — | — | — |
| | | | Polymers (0.35) + Arosurf MSF + R.O. water | 5.0 gal | 96.7 | 100 | — | — | — | — | — |
| | | | Arosurf MSF + well water | 5.0 gal | 73.3 | 76.7 | 86.7 | 100 | — | — | — |
| | | | Arosurf MSF | 0.26 gal | 53.3 | 80 | 90 | 100 | — | — | — |
| 3c | A.T. (25% seawater) | 4th | Control | — | 0 | 0 | 0 | 0 | — | — | — |
| | | | Polymers (0.35) + Arosurf MSF + R.O. water | 5.0 gal | 100 | — | — | — | — | — | — |
| | | | Arosurf MSF + well water | 5.0 gal | 90 | 90 | 93.3 | 100 | — | — | — |
| | | | Arosurf MSF | 0.26 gal | 56.7 | 63.3 | 70 | 100 | — | — | — |
| 3d | A.T. (75% seawater) | 4th | Control | — | 3.3 | 3.3 | 3.3 | 3.3 | — | — | — |
| | | | Polymers (0.35) + Arosurf MSF + R.O. water | 5.0 gal | 100 | — | — | — | — | — | — |
| | | | Arosurf MSF + well water | 5.0 gal | 93.3 | 93.3 | 100 | — | — | — | — |
| | | | Arosurf MSF | 0.26 gal | 60 | 83.3 | 93.3 | 100 | — | — | — |
| 4a | A.T. (0% seawater) | 4th | Control | — | 0 | 0 | 0 | 0 | — | — | — |
| | | | Polymers (0.4) + Arosurf MSF + R.O. water | 5.0 gal | 63.3 | 100 | — | — | — | — | — |
| | | | Polymers (0.6) + Arosurf MSF + well water | 5.0 gal | 70 | 96.7 | 100 | — | — | — | — |
| | | | Arosurf MSF + R.O. water | 5.0 gal | 66.7 | 90 | 100 | — | — | — | — |
| | | | Arosurf MSF | 0.26 gal | 43.3 | 96.7 | 100 | — | — | — | — |
| 4b | A.T. (100% seawater) | 4th | Control | — | 0 | 0 | 6.7 | — | — | — | — |
| | | | Polymers (0.4) + Arosurf MSF + R.O. water | 5.0 gal | 96.7 | 96.7 | 100 | — | — | — | — |
| | | | Polymers (0.6) + Arosurf MSF + well water | 5.0 gal | 86.7 | 96.7 | 100 | — | — | — | — |
| | | | Arosurf MSF + R.O. water | 5.0 gal | 100 | — | — | — | — | — | — |
| | | | Arosurf MSF | 0.26 gal | 40 | 63.3 | 96.7 | 100 | — | — | — |
| 5 | A.T. (100% seawater) | 4th | Control | — | 0 | 0 | 6.7 | 6.7 | — | — | — |
| | | | Polymers (0.4) + Arosurf MSF + R.O. water | 5.0 gal | 56.7 | 96.7 | 96.7 | 100 | — | — | — |
| | | | Arosurf MSF + R.O. water | 5.0 gal | 83.3 | 83.3 | 86.7 | 93.3 | 100 | — | — |
| | | | Arosurf MSF | 0.26 gal | 53.3 | 76.7 | 86.7 | 100 | — | — | — |
| 6 | A.T. (100% seawater) | 4th | Control | — | 0 | 3.3 | 6.7 | 6.7 | 6.7 | — | — |
| | | | Polymers (0.4) + Arosurf MSF + R.O. water | 5.0 gal | 83.3 | 93.3 | 100 | — | — | — | — |
| | | | Arosurf MSF + R.O. water | 5.0 gal | 90 | 90 | 100 | — | — | — | — |

TABLE I-continued

Efficacy of Superabsorbent polymer-base suspensions of Arosurf ® MSF and water against larvae and pupae of *Aedes taeniorhynchus* (A.T.) and *Culex quinquefasciatus* (C.Q.) as related to habitat and formulation water quality[1]

| Test no. | Species (habitat water quality) | Larval instar/ pupae(P) | Formulation[2] (% polymers) | Application rate per surface acre[3,4] | Cumulative percentage mortality of larvae, pupae and/or emerging adults at indicated posttreatment time period (days) | | | | | | |
|---|---|---|---|---|---|---|---|---|---|---|---|
| | | | | | 1 | 2 | 3 | 4 | 5 | 6 | 7 |
| | | | Arosurf MSF | 0.26 gal | 66.7 | 86.7 | 96.7 | 100 | — | — | — |
| | | | Control | — | 0 | 0 | 0 | 0 | — | — | — |
| 7 | A.T. (100% seawater) | 4th/P | Polymers (0.4) + Arosurf MSF + R.O. water | 5.0 gal | 70 | 83.3 | 100 | — | — | — | — |
| | | | Arosurf MSF + R.O. water | 5.0 gal | 96.7 | 96.7 | 100 | — | — | — | — |
| | | | Arosurf MSF | 0.26 gal | 83.3 | 93.3 | 100 | — | — | — | — |
| | | | Control | — | 6.7 | 10 | 10 | — | — | — | — |
| 8 | C.Q. (sewage) | 2nd | Polymers (0.35) + Arosurf MSF + R.O. water | 5.0 gal | 100 | — | — | — | — | — | — |
| | | | Polymers (0.35) + Arosurf MSF + R.O. water | 10.0 gal | 100 | — | — | — | — | — | — |
| | | | Arosurf MSF + R.O. water | 5.0 gal | 86.7 | 90 | 90 | 90 | 96.7 | 100 | — |
| | | | Arosurf MSF + R.O. water | 10.0 gal | 100 | — | — | — | — | — | — |
| | | | Arosurf MSF + well water | 5.0 gal | 86.7 | 96.7 | 96.7 | 96.7 | 100 | — | — |
| | | | Arosurf MSF + well water | 10.0 gal | 100 | — | — | — | — | — | — |
| | | | Arosurf MSF | 0.26 gal | 100 | — | — | — | — | — | — |
| | | | Arosurf MSF | 0.52 gal | 96.7 | 96.7 | 96.7 | 96.7 | 100 | — | — |
| | | | Control | — | 0 | 0 | 0 | 0 | 0 | — | — |
| 9 | C.Q. (R.O.) | 3rd | Polymers (0.4) + Arosurf MSF + R.O. water | 5.0 gal | 13.3 | 20 | 76.7 | 86.7 | 100 | — | — |
| | | | Polymers (0.6) + Arosurf MSF + well water | 5.0 gal | 53.3 | 60 | 90 | 100 | — | — | — |
| | | | Arosurf MSF + R.O. water | 5.0 gal | 20 | 23.3 | 73.3 | 100 | — | — | — |
| | | | Arosurf MSF | 0.26 gal | 6.7 | 13.3 | 70 | 93.3 | 100 | — | — |
| | | | Control | — | 3.3 | 3.3 | 3.3 | 3.3 | 3.3 | — | — |
| 10 | C.Q. (sewage) | 4th | Polymers (0.35) + Arosurf MSF + R.O. water | 5.0 gal | 23.3 | 26.7 | 43.3 | 86.7 | 100 | — | — |
| | | | Polymers (0.35) + Arosurf MSF + R.O. water | 10.0 gal | 40 | 40 | 46.7 | 90 | 100 | — | — |
| | | | Arosurf MSF + R.O. water | 5.0 gal | 16.7 | 23.3 | 50 | 90 | 100 | — | — |
| | | | Arosurf MSF + R.O. water | 10.0 gal | 23.3 | 23.3 | 36.7 | 96.7 | 100 | — | — |
| | | | Arosurf MSF + well water | 5.0 gal | 36.7 | 36.7 | 46.7 | 96.7 | 100 | — | — |
| | | | Arosurf MSF + well water | 10.0 gal | 53.3 | 53.3 | 60 | 100 | — | — | — |
| | | | Arosurf MSF | 0.26 gal | 0 | 0 | 26.7 | 86.7 | 100 | — | — |
| | | | Arosurf MSF | 0.52 gal | 6.7 | 13.3 | 26.7 | 90 | 100 | — | — |
| | | | Control | — | 0 | 0 | 3.3 | 3.3 | 3.3 | — | — |

[1]Starch, acrylonitrile co-polymer (Super Sorb) used in all tests. Arosurf ® MSF lot no. 4158k used in all tests.
[2]All formulations prepared on test day.
[3]Active ingredient in all superabsorbent polymer-base aqueous formulations applied at the rate of ca. 0.26 and 0.52 gal/acre for a total application rate of 5 and 10 gal/acre, respectively.
[4]Active ingredient in aqueous formulations applied at the rate of ca. 0.26 and 0.52 gal/acre for a total formulation application of 5 and 10 gal/acre, respectively.

What I claim is:

1. A controlled release variable-viscosity, flowable insecticidal delivery composition for controlling a population of aquatic environment insects in preflood or flood conditions comprising:
  (a) at least one superabsorbent solid organic polymer comprising hydrophilic acrylamide or acrylate polymers, co-polymers or ter-polymers which absorb over 100 times their weight in water,
  (b) at least one insecticidal agent, and
  (c) water or oil, said polymer, agent and water or oil being present as a flowable formulation wherein the agent is present in a total amount effective to control the population of aquatic environment insects and wherein said composition is an admixture formed by mixing the superabsorbent polymer, the insecticidal agent, and the water or oil.

2. The composition of claim 1, wherein the variable-viscosity, flowable formulation is formed by vigorous or high-shear mixing, and the superabsorbent polymer is substantially water-insoluble.

3. The composition of claim 2, wherein said superabsorbent polymer comprises a starch graft polymer, co-polymer or ter-polymer.

4. The composition of claim 1, wherein said superabsorbent polymer is selected from the group consisting of: an acrylamide sodium acrylate co-polymer; a hydrolyzed starch-polyacrylonitrile; 2-propenenitrile, homopolymer, hydrolyzed, sodium salt, poly (acrylamide-co-sodium acrylate); poly (2-propenamide-co-2-propenoic acid, sodium salt); starch-g-poly (acrylonitrile); starch-g-poly (acrylamide-co-sodium acrylate); a starch, acrylonitrile co-polymer; poly-2-propenoic acid, sodium salt; poly(2-propenamide-co-2-propenoic acid, sodium salt); starch-g-poly(2-propenamide-co-2-propenoic acid, potassium salt); starch-g-poly(2-propenamide-co-2-propenoic acid); starch-g-poly(2-propenamide-co-2-propenoic acid, sodium salt); starch-g-poly(2-propenamide-co-2-propenoic acid sodium/aluminum mixed salts); starch grafted sodium polyacrylates; copolymer acrylamide acrylate; acrylic acid polymers, sodium salt; cellulosic laminates of poly-2-propenoic acid, sodium salt; crosslinked polyacrylamide copolymer; crosslinked modified polyacrylamide; crosslinked acrylics; mixtures thereof; and metal salts thereof.

5. The composition of claim 1, wherein the variable-viscosity, flowable formulation is formed by an additive amount of an electrolyte/salt, in the absence of vigorous or high-shear mixing.

6. The composition of claim 1, wherein said agent comprises at least one compound selected from the group consisting of: avicides; larvicides; pupicides; insecticides; pesticides, toxicants; biological control agents; microbial control agents; pathogens; parasites; chemosterilants; film-forming or surface-active agents; and insect growth regulators.

7. The composition of claim 1, wherein the ratio of superabsorbent polymer to water is from about 0.001:100 to 1:1.

8. A controlled release variable-viscosity, flowable mosquitocidal delivery composition for controlling a population of aquatic environment mosquitoes comprising: at least one superabsorbent solid organic polymer selected from the group consisting of hydrophilic acrylamide and acrylate polymers, co-polymers and terpolymers which absorb over 100 times their weight in water, at least one insecticidal agent comprising a film-forming agent, and at least one additional compound selected from the group consisting of avicides; larvicides; pupicides; insecticides; pesticides; toxicants; chemosterilants; biological control agents; microbial control agents; pathogens; herbicides; attractants; repellents; pheromones; alcohols; and solvents, said composition being in the form of a flowable, aqueous- or oil-base formulation, wherein said polymer, agent and additional compounds are present in a total amount effective to control the population of aquatic environment mosquitoes and wherein said composition is an admixture formed by mixing the superabsorbent polymer, the insecticidal agent, the additional agent and water or oil.

9. The composition of claim 8, wherein the ratio of superabsorbent polymer to water is from about 0.01:100 to about 0.5:1.

10. The composition of claim 9, wherein said superabsorbent polymer is selected from the group consisting of: an acrylamide sodium acrylate co-polymer; a hydrolyzed starch-polyacrylonitrile; 2-propenenitrile, homopolymer, hydrolyzed, sodium salt; poly(acrylamide-co-sodium acrylate); poly(2-propenamide-co-2-propenoic acid, sodium salt); starch-g-poly(acrylonitrile); starch-g-poly(acrylamide-co-sodium acrylate); a starch, acrylonitrile co-polymer; poly-2-propenoic acid, sodium salt; poly(2-propenamide-co-2-propenoic acid, sodium salt); starch-g-poly(2-propenamide-co-2-propenoic acid, potassium salt); starch-g-poly(2-propenamide-co-2-propenoic acid, starch-g-poly(2-propenamide-co-2-propenoic acid, sodium salt); starch-g-poly(2-propenamide-co-2-propenoic acid, sodium/aluminum mixed salt); starch grafted sodium polyacrylates; copolymer acrylamide acrylate; acrylic acid polymers, sodium salt; cellulosic laminates of poly-2-propenoic acid, sodium salt; crosslinked polyacrylamide copolymers; crosslinked modified polyacrylamide; crosslinked acrylics; mixtures thereof and metal salts thereof.

11. The composition of claim 6 wherein said agent further comprises at least one of the group selected from herbicides; attractants; repellents; pheromones; alcohols; solvents; and surfactants.

* * * * *

UNITED STATES PATENT AND TRADEMARK OFFICE
CERTIFICATE OF CORRECTION

PATENT NO. : 4,985,251
DATED : January 15, 1991
INVENTOR(S) : Richard Levy

It is certified that error appears in the above-identified patent and that said Letters Patent is hereby corrected as shown below:

On the title page, Item [75]

Column 1, line 5, at [75] "Meyers" should be --Myers--.

Column 1, line 7, at [73] "Meyers" should be --Myers--.

IN OTHER PUBLICATIONS:

Column 1, line 9, after "Rohm" insert --and--.

Column 2, line 21, change "Taeiorhynchus" to --taeiorhynchus--;

line 23, after "1987." insert --Klier et al., "Solute and Penetrant Diffusion in Swellable Polymers, VIII. Influence of the Swelling Interface Number on Solute Concentration Profiles and Release," *Journal of Controlled Release*, 7 (1988) 61-68.--;

UNITED STATES PATENT AND TRADEMARK OFFICE
CERTIFICATE OF CORRECTION

PATENT NO. : 4,985,251
DATED : January 15, 1991
INVENTOR(S) : Richard Levy

It is certified that error appears in the above-identified patent and that said Letters Patent is hereby corrected as shown below:

line 28, change "(lemna minor)" to --(Lemna minor)"; and line 61, change "Plant" to --Planting--.

Page 3, Column 1, line 5, change "Giganteum" to --giganteum--;

line 19, change "Thuringiensis Var. Is-" to --thuringiensis var. is---;

line 20, change "Sphaericus" to --sphaericus--;

line 23, change "Thuringi-" to --thuringi---;

line 24, change "Var. Israelensis, Bacillus Sphaericus" to --var. israelensis, Bacillus sphaericus--;

line 45, change "Thu-" to --thu---;

UNITED STATES PATENT AND TRADEMARK OFFICE
CERTIFICATE OF CORRECTION

PATENT NO. : 4,985,251
DATED : January 15, 1991
INVENTOR(S) : Richard Levy

Page 3 of 10

It is certified that error appears in the above-identified patent and that said Letters Patent is hereby corrected as shown below:

line 48, change "Thuringiensis" to --thuringiensis--;

line 51, change "Bactimos" to --Bactimos®--;

line 54, change "Bioeegradation" to --Biodegradation--; and lines 56 and 57, change "Edisol-m, EM-1100, QSA 2000 and Mono-Sol" to --"Edisol-m", "EM-1100", "QSA 2000" and "Mono-Sol"--.

Column 2, line 14, change "502S" to --502s--;

line 32, after "Film" insert --)--;

line 45, change "Taeniarhynchus" to --taeniorhynchus--; and line 49, change "Sphaericus" to --sphaericus--;

UNITED STATES PATENT AND TRADEMARK OFFICE
CERTIFICATE OF CORRECTION

PATENT NO. : 4,985,251
DATED : January 15, 1991
INVENTOR(S) : Richard Levy It is certified that error appears in the above-identified patent and that said Letters Patent is hereby corrected as shown below:

line 50, change "Quinguefasciatus" to --quinquefasciatus--.

Page 4, Column 1, line 2, change "Thu-" to --thu---;

line 3, change "Israelensis" to --israelensis--and delete "the";

change "Psorophora" to --Psorophora--; and line 23, change "Quadrimaculatus" to --quadrimaculatus--.

Column 2, line 5, change "Aro-surf" to --Arosurf--;

lines 8 and 9, change "Entomology in Human and Animal Health" to --Entomology in Human and Animal Health--;

line 12, change "Kyeonieus" to --Kydonieus--.

UNITED STATES PATENT AND TRADEMARK OFFICE
CERTIFICATE OF CORRECTION

PATENT NO. : 4,985,251
DATED : January 15, 1991
INVENTOR(S) : Richard Levy It is certified that error appears in the above-identified patent and that said Letters Patent is hereby corrected as shown below:

Column 2, lines 8-11, change "Aedes, Anopheles, Culex, Culiseta, Coquillettidia, Deinocerites, Mansonia, Orthopodomyia, Psorophora, Uranotaenia and Wyeomyia" to --Aedes, Anopheles, Culex, Culiseta, Coquillettidia, Deinocerites, Mansonia, Orthopodomyia, Psorophora, Uranotaenia and Wyeomyia--; and line 13, change "states" to --stages--.

Column 4, line 7, change "israelensis" to --israelensis--;

line 18, after "application" delete ".";

line 20, change "2:233-236.)" to --2:233-236).--;

line 60, change "israelensis" to --israelensis--; and

UNITED STATES PATENT AND TRADEMARK OFFICE
CERTIFICATE OF CORRECTION

PATENT NO. : 4,985,251
DATED : January 15, 1991
INVENTOR(S) : Richard Levy

It is certified that error appears in the above-identified patent and that said Letters Patent is hereby corrected as shown below:

line 63, change "(BSP-1)" to --(e.g., BSP-1)--.

Column 5, line 22, change "Specific Objects" to --3. Specific Objects--; and line 48, before "Specific Aspects" insert --4.--.

Column 7, line 39, before "Specific Advantages" insert --5.--.

Column 9, line 58, change "ra-Sorb" to --ra-Sorb$^{TM}$--;

line 59, change "Terra-Sorb" to --Terra-Sorb$^{TM}$--;

line 64, change "starch-g-poly (2-propenamide" to --starch-g-poly(2-propenamide--;

line 67, change "starch-g-poly (2-propenamide" to --starch-g-poly(2-propenamide--; and

UNITED STATES PATENT AND TRADEMARK OFFICE
CERTIFICATE OF CORRECTION

PATENT NO. : 4,985,251
DATED : January 15, 1991
INVENTOR(S) : Richard Levy

It is certified that error appears in the above-identified patent and that said Letters Patent is hereby corrected as shown below:

line 68, after "acid" insert --, sodium salt--.

Column 10, line 1, change "starch-g-poly (2-propenamide-co-2 -propenoic" to --starch-g-poly (2-propenamide-co-2-propenoic--;

line 4, change "starch-g-poly (2-propenamide" to --starch-g-poly(2-propenamide--;

line 5, change "salt" to --salts--;

line 15, change "sodium    acrylate)," to --sodium acrylate),--;

line 16, change "5025" to --502s--;

line 19, change "cross-linked" to --crosslinked--;

line 21, change "cross-linked" to --crosslinked--; and

UNITED STATES PATENT AND TRADEMARK OFFICE
CERTIFICATE OF CORRECTION

PATENT NO. : 4,985,251
DATED : January 15, 1991
INVENTOR(S) : Richard Levy

Page 8 of 10

It is certified that error appears in the above-identified patent and that said Letters Patent is hereby corrected as shown below:

line 45, after "bonding" insert --of water with superabsorbent polymers--.

Column 13, line 4, change "Lacenidium" to --Lagenidium--; and line 47, change "Mansonia" to --Mansonia-- and change "Coquillettidia" to --Coquillettidia--.

Column 16, lines 20 and 21, delete "replaced with" and insert --and--; and line 66, change "ar" to --are--.

Column 17, line 4, change "high" to --high-shear--.

Column 18, line 2, after "cosity" delete "."; and line 4, after "flowable" insert --,--.

Column 19, line 16, change "wa" to --was--; and line 48, change title "EXAMPLE III" to be centered above the following text.

UNITED STATES PATENT AND TRADEMARK OFFICE
CERTIFICATE OF CORRECTION

PATENT NO. : 4,985,251
DATED : January 15, 1991
INVENTOR(S) : Richard Levy

It is certified that error appears in the above-identified patent and that said Letters Patent is hereby corrected as shown below:

Column 21, lines 21-22, change "post-treatment" to --posttreatment--.

IN THE TABLES:

Table 1, Column 21, line 1, change "Superabsorbent" to --superabsorbent--.

Column 23, line 1, change "Superabsorbent" to --superabsorbent--.

Column 24, line 21, change "5.67" to --56.7--.

IN THE CLAIMS:

Claim 4, Column 26, line 45, change "salt," to --salt;--;

line 51, after "salt);" delete spaces and insert only 1 space;

line 55, after "acid" insert --,--; and line 68, change "avicides" to --ovicides--.

Claim 6, Column 27, line 1, change "pesticides," to --pesticides;--;

UNITED STATES PATENT AND TRADEMARK OFFICE
CERTIFICATE OF CORRECTION

PATENT NO. : 4,985,251
DATED : January 15, 1991
INVENTOR(S) : Richard Levy It is certified that error appears in the above-identified patent and that said Letters Patent is hereby corrected as shown below:

line 17, change "avicides" to --ovicides--; and line 20, before "herbicides" insert --parasites; insect growth regulators--.

Claim 10, Column 28, line 14, after "salt);" delete the spacing and insert 1 space;

line 16, delete "acid," and insert --acid);--; and line 19, change "salt" to --salts--.

Signed and Sealed this

Twenty-fourth Day of August, 1993

*Attest:*

BRUCE LEHMAN

*Attesting Officer*     *Commissioner of Patents and Trademarks*